US011439455B2

(12) United States Patent
Shavit

(10) Patent No.: US 11,439,455 B2
(45) Date of Patent: Sep. 13, 2022

(54) SYSTEM, DEVICE AND METHOD FOR INTRADERMAL SOLUTION DELIVERY

(71) Applicant: Novoxel Ltd., Netanya (IL)

(72) Inventor: Ronen Shavit, Tel Aviv (IL)

(73) Assignee: Novoxel Ltd., Netanya (IL)

( * ) Notice: Subject to any disclaimer, the term of this patent is extended or adjusted under 35 U.S.C. 154(b) by 279 days.

(21) Appl. No.: 16/498,230

(22) PCT Filed: Mar. 27, 2018

(86) PCT No.: PCT/IL2018/050350
§ 371 (c)(1),
(2) Date: Sep. 26, 2019

(87) PCT Pub. No.: WO2018/178976
PCT Pub. Date: Oct. 4, 2018

(65) Prior Publication Data
US 2021/0113258 A1 Apr. 22, 2021

Related U.S. Application Data

(60) Provisional application No. 62/476,963, filed on Mar. 27, 2017.

(51) Int. Cl.
*A61B 18/12* (2006.01)
*A61B 18/08* (2006.01)
*A61B 18/00* (2006.01)

(52) U.S. Cl.
CPC ........ *A61B 18/1206* (2013.01); *A61B 18/082* (2013.01); *A61B 2018/0075* (2013.01);
(Continued)

(58) Field of Classification Search
CPC ............ A61B 2218/00; A61B 2562/00; A61B 18/1206; A61B 18/082;
(Continued)

(56) References Cited

U.S. PATENT DOCUMENTS

| 5,611,806 A | 3/1997 | Jang |
| 5,769,880 A | 6/1998 | Truckai et al. |

(Continued)

FOREIGN PATENT DOCUMENTS

| CN | 106255525 A | 12/2016 |
| EP | 1314400 B1 | 6/2007 |

(Continued)

OTHER PUBLICATIONS

International Search Report for PCT/IL2018/050350, dated Jul. 26, 2018 (4 pages).

(Continued)

*Primary Examiner* — Linda C Dvorak
*Assistant Examiner* — Mystee Nguyen Delgado
(74) *Attorney, Agent, or Firm* — Brown Rudnick LLP

(57) ABSTRACT

A dermal conditioning device for creating at feast one fissure, in a stratum corneum layer of an area of skirt, comprising: a non-invasive fissuring generator; a controller coupled to the non-invasive skin fissuring generator, a power supply coupled to the non-invasive skin fissuring generator and the controller; and a housing encasing the non-invasive skin fissuring generator and the controller, wherein the controller controls the non-invasive skin fissuring generator to: generate at least one signal, and apply the at least one signal to dehydrate the area of skin, and stress the external surface of the stratum corneum layer of the area of skin, the stress calibrated to produce a strain on the stratum corneum layer causing a formation of at least one fissure in the stratum corneum layer when the area of skin is dehydrated, while maintaining a pre-fissure immune status of the area of skin.

22 Claims, 20 Drawing Sheets

(52) U.S. Cl.
CPC ........... *A61B 2018/00202* (2013.01); *A61B 2018/00452* (2013.01); *A61B 2018/00714* (2013.01); *A61B 2018/00732* (2013.01); *A61B 2018/00761* (2013.01); *A61B 2018/00934* (2013.01)

(58) Field of Classification Search
CPC ........... A61B 2018/00202; A61B 2018/00452; A61B 2018/00714; A61B 2018/00732; A61B 2018/0075; A61B 2018/00761; A61B 2018/00934; A61B 2018/00196; A61B 2018/0047; A61B 2018/143; A61B 2018/00642; A61B 2018/00613; A61B 2018/00625; A61B 2018/00636; A61B 2018/00696; A61B 2018/00791; A61B 2018/00827; A61B 2018/00779; A61B 2017/00747; A61B 2017/00765; A61B 2018/00005; A61B 2018/0016; A61B 5/441; A61B 5/4839; A61B 2018/00702; A61B 2018/00767; A61M 35/00; A61M 37/00; A61M 37/0015; A61M 2037/0007; A61N 5/0616; A61Q 19/007; A61Q 19/005

See application file for complete search history.

(56) References Cited

U.S. PATENT DOCUMENTS

| | | | |
|---|---|---|---|
| 6,468,508 | B1 | 10/2002 | Laughlin |
| 6,527,716 | B1 | 3/2003 | Eppstein |
| 6,595,947 | B1 | 7/2003 | Mikszta et al. |
| 6,881,212 | B1 | 4/2005 | Clement et al. |
| 7,758,537 | B1 | 7/2010 | Brunell et al. |
| 7,758,561 | B2 | 7/2010 | Eppstein |
| 9,044,582 | B2 * | 6/2015 | Chang ............... A61N 1/325 |
| 9,579,380 | B2 | 2/2017 | Eppstein |
| 2002/0058936 | A1 | 5/2002 | Avrahami et al. |
| 2002/0065533 | A1 * | 5/2002 | Weaver .............. A61M 37/00 606/191 |
| 2004/0260234 | A1 | 12/2004 | Srinivasan et al. |
| 2006/0047281 | A1 * | 3/2006 | Kreindel ............. A61B 18/18 606/49 |
| 2009/0130223 | A1 | 5/2009 | Breitenbach et al. |
| 2009/0156958 | A1 | 6/2009 | Mehta et al. |
| 2011/0060270 | A1 | 3/2011 | Eppstein |
| 2011/0178456 | A1 | 7/2011 | Aguilar-Mendoza et al. |
| 2012/0109041 | A1 | 5/2012 | Munz |
| 2016/0317208 | A1 * | 11/2016 | Slatkine ............. A61B 18/08 |
| 2016/0331440 | A1 * | 11/2016 | Slatkine ............. A61B 18/08 |
| 2017/0043154 | A1 | 2/2017 | Pelssers et al. |

FOREIGN PATENT DOCUMENTS

| | | |
|---|---|---|
| JP | 2-309973 | 12/1990 |
| JP | 2004-533296 A | 11/2004 |
| JP | 2017-501825 A | 1/2017 |
| JP | 2017-503564 A | 2/2017 |
| WO | 2016042546 A2 | 3/2016 |
| WO | WO-2016042546 A2 * | 3/2016 ............. A61B 18/08 |

OTHER PUBLICATIONS

Written Opinion for PCT/IL2018/050350, dated Jul. 26, 2018 (7 pages).
https://www.youtube.com/watch?v=e_mXpqQCEB0, May 24, 2016, the whole video.
Kriwet, K. & Müller-Goymann, C.C., Binary diclofenac diethylamine-water systems, micelles, vesicles, and lyotropic liquid crystals. Eur J. Pharm. Biopharm. 39, 234 238,1993.
Singh, P., et al, Facilitated transdermal delivery by iontophoresis, In: Bronaugh, R.L., Maibach, H.I. (Eds.), Percutaneous Absorption, Drugs- Cosmetics-Mechanisms-Methodology . . . 3rd ed. Marcel Dekker Inc., New York, pp. 333-657, 1999.
Smith, E.W. & Maibach, H.I., Percutaneous Penetration Enhancers. CRC Press, Boca Raton, FL, 1995.
Wildnauer et al., Stratum Corneum Biomechanical Properties I. Influence of Relative Humidity on Normal and Extracted Human Stratum Corneum, Journal of Investigative Dermatology, vol. 56, No. 1, Jan. 1, 1971, pp. 72-78.
Barry, B.W., Novel mechanisms and devices to enable successful transdermal drug delivery. Europ. J. Pharm. Sci. 14, 101-114, 2001.
Ben-Shabat, S. et al, Conjugates of unsaturated fatty acids with propylene glycol as potentially less-irritant skin penetration enhancers. Drug Dev. Ind. Pharm. 33, 1169-1175, 2007.
Davis, A.F. et al, Formulation strategies for modulating skin penetration. In: Walters, K.A. (Ed.), Dermatological and Transdermal Formulations . . . Marcel Dekker Inc, New York, pp. 271-317, 2002.
Egawa M et al, , In vivo Estimation of Stratum Corneum Thickness from Water Concentration Profiles Obtained with Raman Spectroscopy, Acta Derm Venereol; 87:4-8, 2007.
Elford EL & Bedi VPI, Enhanced Skin Permeability of Ascorbic Acid after Clear + Brilliant Permea Laser Treatment, Aug. 2012.
Elman, M. et al, Fractional treatment of aging skin with tixel, a clinical and histological 30 evaluation. J. Cosmet. Laser Ther. 20, 1-7, 2016.
Farris, P.K., Topical vitamin C: a useful agent for treating photoaging and other dermatologic conditions. Dermatol. Surg. 31, 814-817 (review), 2005.
Giuliano, F. & Warner, T.D., Ex vivo assay to determine the cyclooxygenase selectivity of non-steroidal anti-inflammatory drugs. Br. J. Pharmacol. 126, 1824-1830, 1999.
Greenfield, J.M. et al, Verapamil versus saline in 5 electromotive drug administration for Peyronie's disease: a double-blind, placebo controlled trial. J. Urol. 177, 972-975, 2007.
Guy, R.H. et al, Iontophoretic transport across the skin. Skin Pharmacol. Appl. Skin Physiol. 14, 35-40, 2001.
Henry, S. et al, Microfabricated 10 microneedles: a novel approach to transdermal drug. J. Pharm. Sci. 87, 922-925, 1998.
Hu, Q. et al, Enhanced transdermal delivery of tetracaine by electroporation. Int. J. Pharm. 202, 121-124, 2000.
Kaur, M. et al, Microneedle-assisted 15 delivery of verapamil hydrochloride and amlodipine besylate. Europ. J. Pharm. Biopharm. 86, 284-291 ,2014.
Kriwet, K. & Müller-Goymann, C.C., Diclofenac release from phospholipid drug systems and permeation through excised human stratum corneum. Int. J. Pharm. 125, 231-242, 1995.
Lask, G. et al, Fractional vaporization of tissue with an oscillatory array of high temperature rods Part I: ex vivo study. 25 J. Cosmet. Laser Ther. 5, 218-223, 2012.
Lee, J.W. et al, Microsecond thermal ablation of skin for transdermal drug delivery. J. Control. Release 54, 58-68, 2011.
Legato II Brochure.
Levine, L.A et al, Experience with intraplaque injection of verapamil for Peyronie's Disease. J. Urol. 168, 621-626, 2002.
Marro, D., et al., Characterization of the iontophoretic permselectivity properties of human and pig skin. J. Control. Release 70, 213-217, 2001.
McAllister, D.V., et al, Microfabricated microneedles for gene and drug delivery. Ann. Rev. Biomed. Eng. 2, 298-313, 2000.
Ogura, M et al, Low frequency sonophoresis: current status and future prospects. Adv. Drug Delivery Rev. 60, 1218-1223, 2008.
Park, J.H. et al, The effect of heat on skin permeability. Int. J. Pharm. 359, 94-103, 2008.
Prausnitz, M.R. et al., Electroporation of mammalian skin: a mechanism to enhance transdermal drug delivery. Proc. Natl. Acad. Sci U. S. A. 90, 10504-10508, 1993.
Prausnitz, M.R., A practical assessment of transdermal drug delivery by skin electroporation. Adv. Drug Delivery Rev. 35, 61-76, 1999.

(56) References Cited

OTHER PUBLICATIONS

Preissig et al, Current Laser Resurfacing Technologies: A Review that Delves Beneath the Surface, Semin Plast Surg 26:109-116, 2012.

Riviere, J.E. et al, Pulsatile transdermal delivery of LHRH using electroporation: drug 15 delivery and skin toxicology. J. Control. Release 36, 229-233 1995.

Sintov, A.C. & Botner, S., Transdermal drug delivery using microemulsion and aqueous systems: influence of skin storage conditions on the in vitro permeability of diclofenac from aqueous vehicle systems. Int. J. Pharm. 311, 55-62, 2006.

Sintov, A.C. & Brandys-Sitton, R., Facilitated skin penetration of lidocaine: 25 combination of a short-term iontophoresis and microemulsion formulation. Int. J. Pharm. 316, 58-67, 2006.

Sintov, A.C. & Greenberg, I., Comparative percutaneous permeation study using caffeine-loaded microemulsion showing low reliability of the frozen/thawed skin models. Int. J. Pharm. 471, 516-524, 2014.

Sintov, A.C. et al, Radiofrequency driven skin microchanneling as a new way for electrically assisted transdermal delivery of hydrophilic drugs. J. Control. Release 89, 311-320, 2003.

Tuygun, C. et al, The effectiveness of transdermal electromotive administration with verapamil and 5 dexamethasone in the treatment of Peyronie's disease. Int. Urol. Nephrol. 41, 113-118, 2009.

Vanbever, R. et al, Transdermal delivery of fentanyl by Electroporation I. Influence of electrical factors. Pharm. Res. 13, 559-565, 1996.

Vanbever, R. et al, Transdermal delivery of metoprolol by electroporation. Pharm. Res. 11, 1657-1662, 1994.

Walters, K.A., Penetration enhancers and their use in transdermal therapeutic systems. In: Hadgraft, J., Guy, R.H. (Eds.), Transdermal Drug Delivery, Developmental Issues and Research Initiatives . . . Marcel Dekker Inc, New York, pp. 197-246, 1989.

Office Action and the English translation issued in Japanese Application No. 2019-552858, dated May 18, 2022, 5 pages.

Chinese Search Report and the English translation issued in Chinese Application No. 2018800253228, dated Jun. 28, 2022, 4 pages.

\* cited by examiner

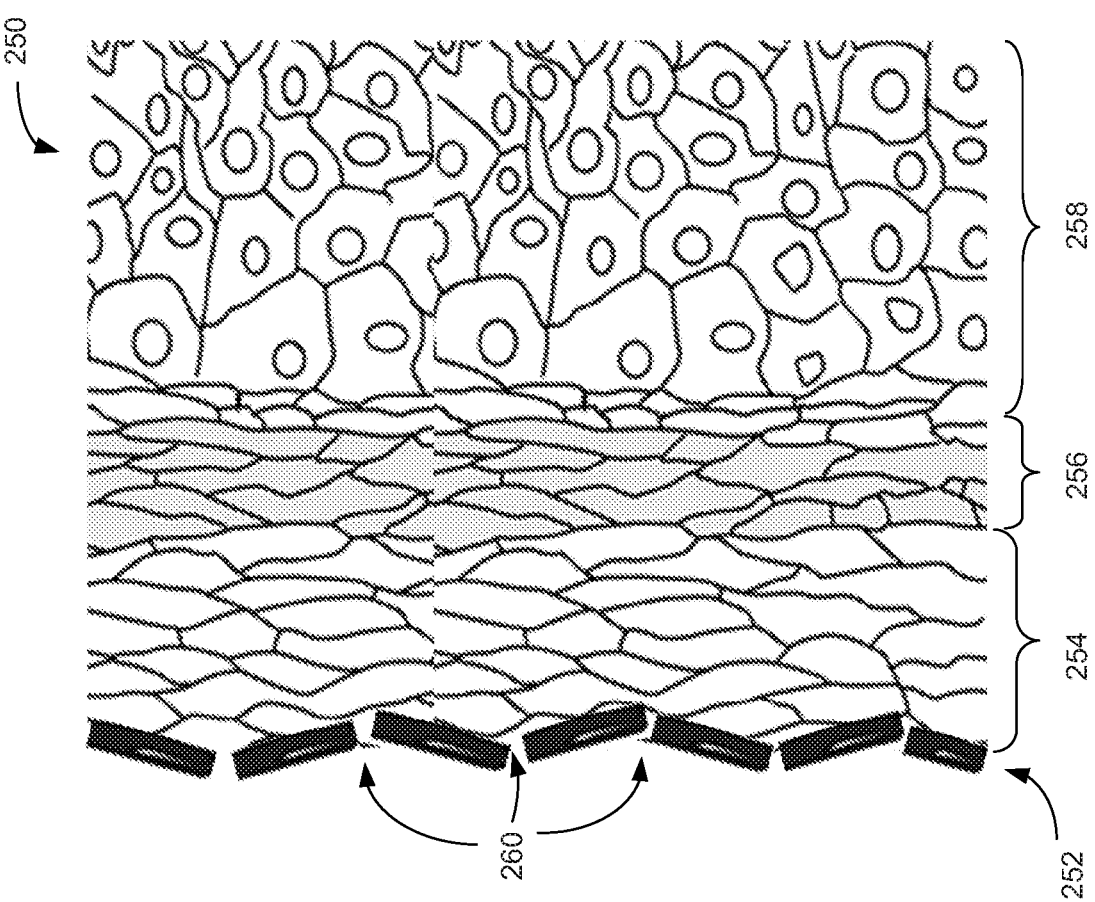
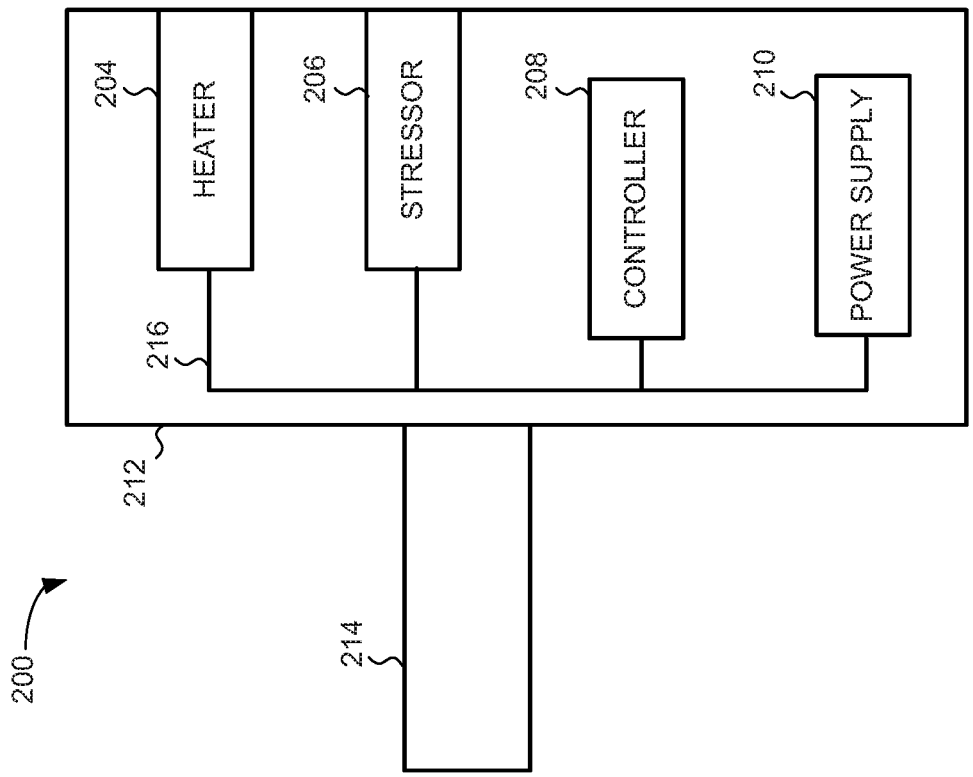
FIG. 2C

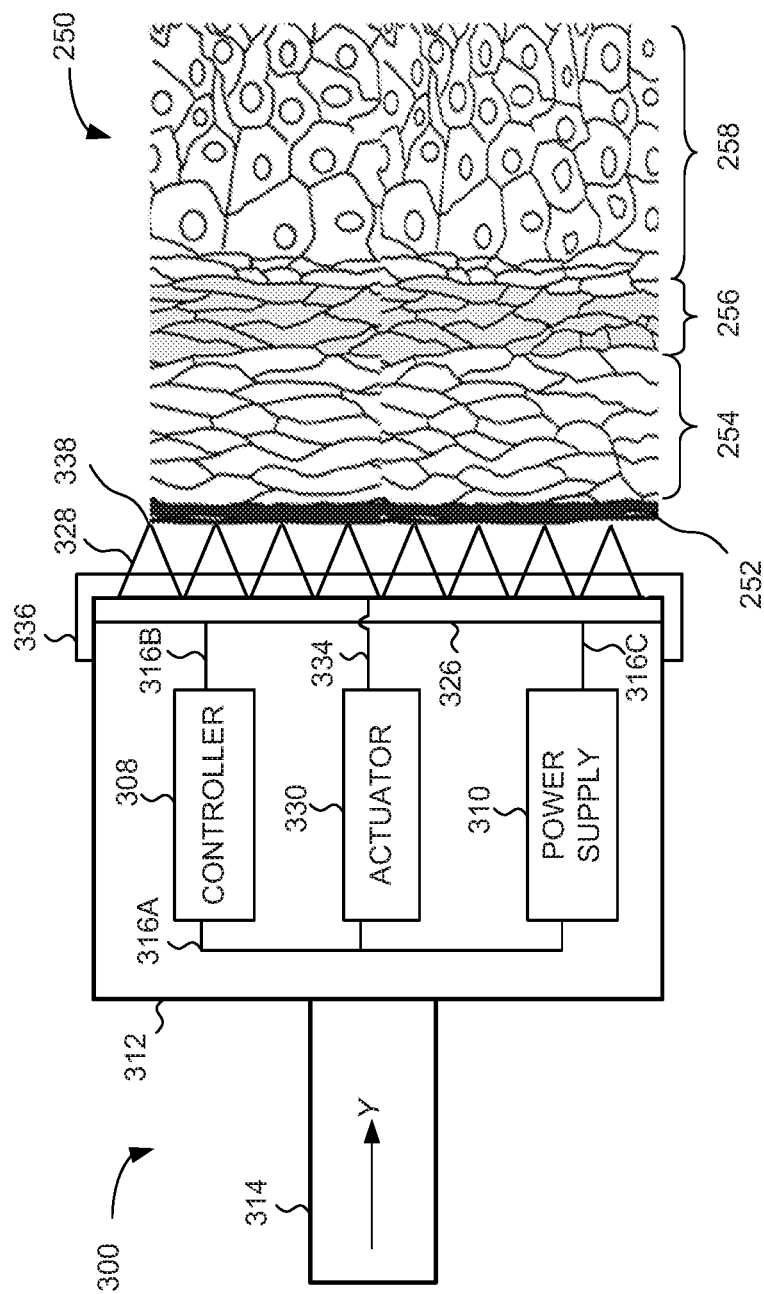

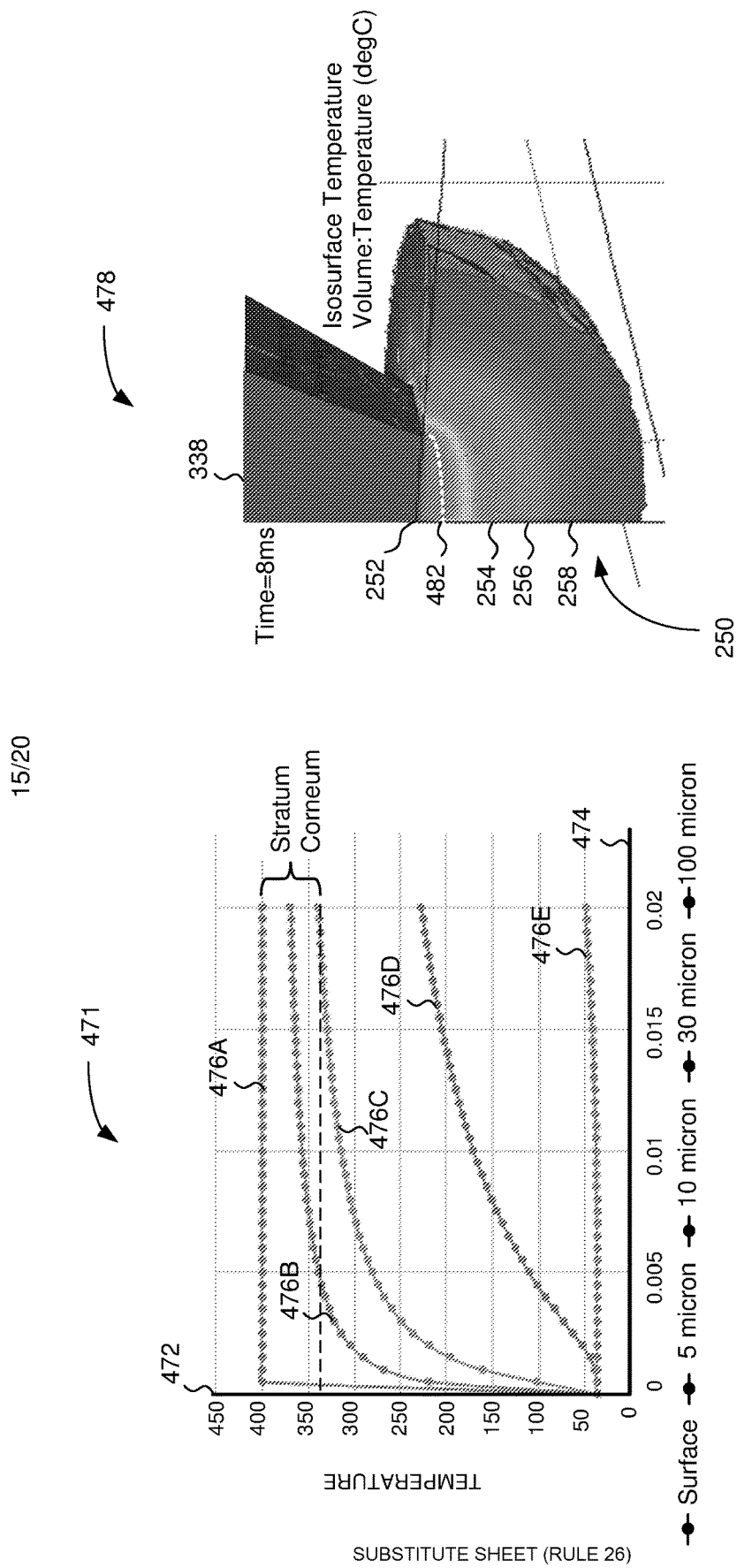

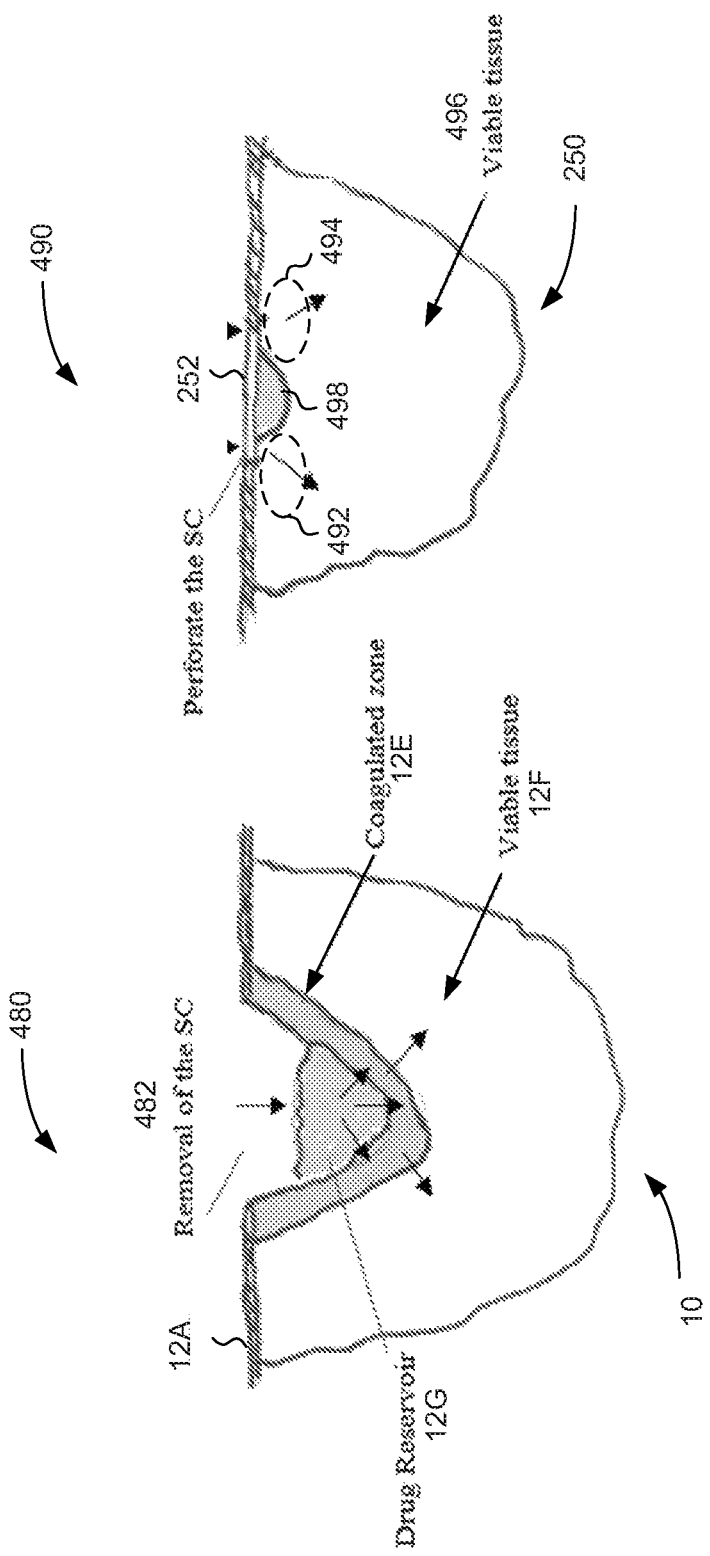

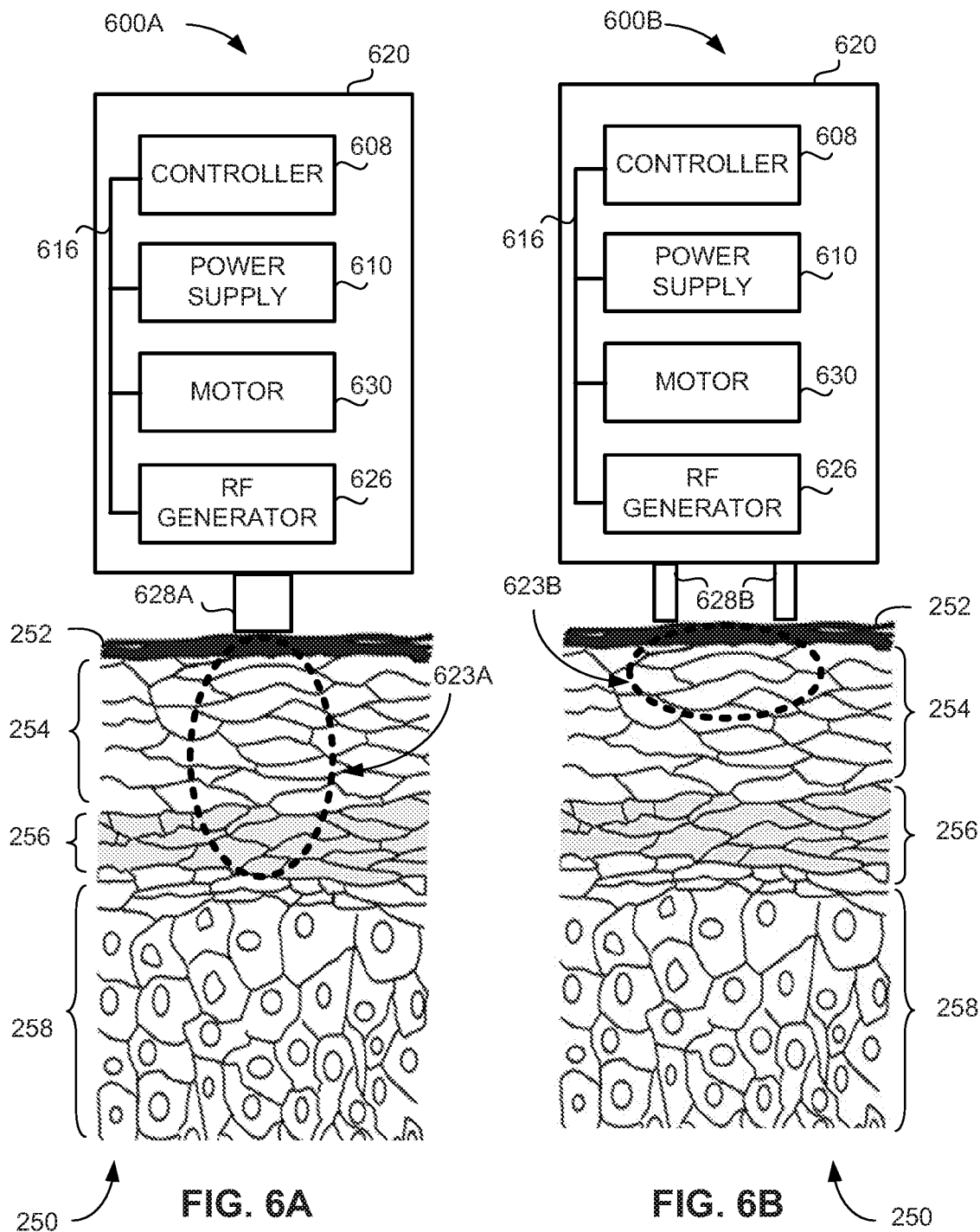

SYSTEM, DEVICE AND METHOD FOR INTRADERMAL SOLUTION DELIVERY

CROSS-REFERENCE TO RELATED APPLICATIONS

The present application is a national stage entry of PCT/IL2018/050350 with an International Filing Date of Mar. 27, 2018, which claims the benefit of and priority to U.S. Provisional Application No. 62/476,963, filed Mar. 27, 2017, the contents of each of which are incorporated by reference herein their entirety.

FIELD OF THE DISCLOSED TECHNIQUE

The disclosed technique relates to systems and methods for intradermal treatment, in general, and to systems and methods for conditioning an area of skin to absorb a solution intradermally applied externally, in particular.

BACKGROUND OF THE DISCLOSED TECHNIQUE

Skin is a dynamic, multi-layered organ in a constant state of change as cells of the uppermost, outer layers are shed and replaced by inner cells moving up to the surface of the skin. Although structurally consistent throughout the body, skin varies in thickness according to anatomical site and age of the individual. Anatomically speaking, the epidermis is the outermost layer, serving as the physical and chemical barrier between the interior body and exterior environment; the dermis is a deeper layer providing structural support for the skin, while the subcutis or hypodermis is a further layer which is an important depot of fat. The dermis is a layer made up of loose connective tissue.

Reference is now made to FIG. 1A, which is a schematic illustration of a cross section of a sample of epidermis, generally referenced 10, as is known in the prior art. Epidermis 10 is a stratified squamous epithelium, the main cells of which are called keratinocytes, which synthesize the protein keratin. Keratinocytes are in a constant state of transition from the deeper skin layers to the uppermost skin layer. Protein bridges called esmosomes connect keratinocytes. Epidermis 10 includes four separate layers formed by keratinocytes in various stages of keratin maturation. Moving from the outermost surface to the deeper layers, the four layers of the epidermis are: an outermost layer 12A, referred to herein as the stratum corneum 12A, a stratum granulosum 128 (also known as the granular cell layer), a stratum spinosum 12C (also known as the spinous or prickle cell layer), and a stratum basale 12D (also known as the basal or germinativum cell layer).

Stratum corneum 12A is made up of layers of hexagonal-shaped, non-viable cornified cells known as corneocytes. In most areas of the skin, there are 10-30 layers of stacked corneocytes. Each corneocyte is surrounded by a protein envelope and is filled with water-retaining keratin proteins. The cellular shape and orientation of the keratin proteins add strength to stratum corneum 12A. Surrounding the cells are stacked layers of lipid bilayers. The resulting structure of stratum corneum 12A provides the natural physical and water-retaining barrier of the skin. The upwards movement of epidermal cells, such from stratum basale 12D to stratum corneum 12A usually takes about 28 days and is known as the epidermal transit time.

Intradermal drug delivery relates to various relatively non-invasive techniques for delivering drugs to the deeper skin layers, i.e. any of the layers lying beneath stratum corneum 12A. Technologies and techniques for intradermal drug delivery fall into two general categories. The first category causes mechanical and physical breaches in the epidermal layers of the skin, such as by causing perforations, ablation or slicing, thereby enabling medication and drugs to be delivered intradermally. The second category chemically changes the properties of the skin, in particular the epidermis, thus causing it to be more receptive to absorbing a drug, ointment or medication. Examples of such techniques include electroporation, external stimulation by the diffusion of substances that cause the dilation of local blood vessels and the like.

Thermo-mechanical ablation (herein abbreviated TMA) is a known technique used in dermatological treatments, wherein the skin is heated to a sufficiently high temperature so as to cause areas of stratum corneum 12A to ablate, i.e. to vaporize. TMA causes the creation of microcraters on the external surface of stratum corneum 12A through which an aqueous solution, such as an ointment, drug or medication, may be delivered to the lower layers of the skin, e.g. to stratum granulosum 12B, stratum spinosum 12C, and stratum basale 12D. Commonly, a laser is used to vaporize stratum corneum 12A, resulting in the creation of the microcraters. However the process of ablation may cause damage, resulting in coagulation and disintegration of the uppermost layers of the skin, the topmost being the papillary dermis. Ablation can thus cause patient discomfort, as well as scarring of the skin tissue, ultimately hampering the effectiveness of the intended absorption in dermatological treatments.

Reference is now made to FIG. 18, which is an image of a sample of skin having undergone an ablative laser treatment, generally referenced 20, as is known in the prior art. In FIG. 18, the various layers of the epidermis are visible, such as stratum corneum 22A, stratum granulosum 228, stratum spinosum 22C and stratum basale 22D. As shown, the ablative laser treatment results in the vaporization of a region of the stratum corneum 22A shown by a circle 24, and the coagulation of a region of deeper skin layers 22B and 22C, shown by a circle 26. The vaporization shown by circle 24 indicates the region where stratum corneum 22A has been vaporized, thereby exposing the tissue below to the surrounding environment. Region 26 (shown encircled) indicates dermal coagulation of the papillary dermis, thereby hampering its absorption capability.

Reference is now made to FIG. 1C, which is an image of a sample of skin having undergone an ablative treatment using a radio frequency (herein abbreviated RF) process, generally referenced 30, as is known in the prior art. Visible in the image are skin layers stratum corneum 32A, stratum granulosum 328, stratum spinosum 32C and stratum basale 32D. Visible as well is a crater 34, indicating a region where stratum corneum 32A has been vaporized, exposing the tissue below. A region 36 (shown encircled) shows an area of burned tissue that has been cauterized as a result of the ablative RF treatment. Due to the cauterization, region 36 is coagulated and poses a secondary permeation barrier between the tissue below and the external surface of skin 30 at crater 34, thus achieving the opposite result of an ablative treatment meant to open up the epidermis to enable intradermal drug delivery. Ablative RF treatments do not always cause cauterization.

Other methods for intradermal drug delivery are known in the art. U.S. Pat. No. 6,595,947 B1 to Mikszta et al., entitled "Topical Delivery of Vaccines" is directed to a method for a topical delivery of a substance to the epidermal tissue of the skin. The method uses abrasion to disrupt the stratum corneum layer of the skin to enable the delivery the substance to the epidermal tissue of the skin. The abrasion disrupts the stratum corneum, without disturbing the epidermis layers.

U.S. Pat. No. 5,611,806 to Jang, entitled "Skin perforating device for transdermal medication" is directed to a device that cuts the skin using multiple needle disks. The needle disks are covered with multiple skin perforating needles. The device causes cuts of uniform depth in the skin that facilitate the delivery of transdermal medication.

The publication "Fractional treatment of aging skin with Tixel, a clinical and histological evaluation" to Elman et al., published in the Journal of Cosmetic and Laser Therapy, 2016, 18(1):31-7, Epub 2016 Jan. 20 (last seen at http://www.ncbi.nlm.nih.gov/pubmed/26073117 on Mar. 12, 2018), discloses a comparison of an intradermal treatment by a TMA-based device referred to as "Tixel" to a $CO_2$ laser treatment for the removal of skin wrinkles using fractional ablation of facial epidermal tissue. The TMA-based device is provided with a metallic tip that is heated to 400° C. and applied to the skin in a series of pulses of varying time lengths and a preset protrusion depth. The publication reports that both treatments caused the creation of craters presenting epidermal evaporation and dermal coagulation of the papillary dermis below the stratum corneum layer.

The publication "A novel thermo-mechanical system enhanced transdermal delivery of hydrophilic active agents by fractional ablation" to Sintov, A. C and Hofmann, M. A., published in the International Journal of Pharmaceutics, Vol. 511, pp. 821-830, 2016, discloses using a TMA-based device having a gold-plated stainless steel tip for investigating a treatment of a sample of porcine ear skin in preparation for the delivery of an aqueous solution. The TMA-based device was used to transfer thermal energy to the surface porcine ear skin. The treatment resulted in the creation of multiple microchannels by vaporizing regions of the stratum corneum layer.

SUMMARY OF THE PRESENT DISCLOSED TECHNIQUE

It is an object of the disclosed technique to provide a novel method and system for conditioning an area of skin for absorbing a solution into the deeper skin layers while maintaining the cellular integrity and viability of the skin tissue, and preserving the penetration barrier function of the skin prior to treatment.

In accordance with the disclosed technique, there is thus provided a dermal conditioning device for creating at least one fissure in a stratum corneum layer of an area of skin. The dermal conditioning device includes: at least one non-invasive skin fissuring generator, at least one controller, a power supply, and a housing. The at least one controller is coupled to the at least on non-invasive skin fissuring generator. The power supply is coupled to the at least one non-invasive skin fissuring generator and the at least one controller. The housing encases the at least one non-invasive skin fissuring generator and the at least one controller. The at least one controller controls the at least one non-invasive skin fissuring generator to: generate at least one signal, and apply the at least one signal to dehydrate the area of skin, and stress the external surface of the stratum corneum layer of the area of skin. The stress is calibrated to produce a strain on the stratum corneum layer of the area of skin. The strain causes a formation of at least one fissure in the stratum corneum layer of the area of skin when the area of skin is dehydrated, while maintaining a pre-fissure immune status of the area of skin.

In some embodiments, the at least one non-invasive skin fissuring generator includes a dehydrating generator selected from the group consisting of: a dry flow generator, a radio frequency generator, an optical emitter, and a thermal heater.

In some embodiments, the at least one non-invasive skin fissuring generator includes a stress applying generator selected from the group consisting of: a dry flow generator, and a radio frequency generator.

In some embodiments, the at least one non-invasive skin fissuring generator includes a motor mechanically coupled to a distal end of the dermal conditioning device, the motor configured to apply the at least one signal to stress the external surface of the stratum corneum layer of the area of skin.

In some embodiments, the motor is configured to perform one of: a) repeatedly push the distal end of the dermal conditioning device distally and retrieve the distal end proximally, and b) rotate a roller at the distal end of the dermal conditioning device.

In some embodiments, the distal end of the device is provided with at least one non-invasive protrusion configured to apply the at least one signal to stress the external surface of the stratum corneum layer of the area of skin.

In some embodiments, the at least one non-invasive protrusion has embedded therein an optical channel, the optical channel configure to apply the at least one signal to dehydrate the area of skin.

In accordance with the disclosed technique, there is thus provided a method for conditioning an area of skin, the method comprising: generating at least one signal, and applying the at least one signal to: dehydrate the area of skin, and stress the external surface of a stratum corneum layer of the area of skin, the stress calibrated to produce a strain on the stratum corneum layer of the area of skin, the strain causing a formation of at least one fissure in the stratum corneum layer of the area of skin when the area of skin is dehydrated, while maintaining a pre-fissure immune status of the area of ski.

In some embodiments, applying the at least one signal to dehydrate the area of skin dehydrates the stratum corneum layer of the area of skin to less than 10% water content.

In some embodiments, applying the at least one signal to dehydrate the area of skin dehydrates a stratum granulosum layer of the area of skin to less than 70% water content.

In some embodiments, generating the at least one signal includes maintaining a distal end of the dermal conditioning device at 400 degrees Celsius.

In some embodiments, generating the at least one signal includes generating a pulse of a duration ranging between 8 milliseconds and 14 milliseconds.

In some embodiments, generating the at least one signal to stress the external surface of the stratum corneum layer of the area of skin comprises applying the stress non-invasively to depress the external surface of the stratum corneum layer to a depth ranging between 0.1 millimeters and 1 millimeter.

In some embodiments, generating the at least one signal includes controlling a first parameter of the at least one signal, the first parameter selected from the group consisting of: a timing, an intensity, a temperature, a frequency, a duration, and a phase, of the at least one signal.

In some embodiments, the method further includes synchronizing the applying the at least one signal to stress the external surface of the stratum corneum layer of the area of skin with the applying the at least one signal to dehydrate the area of skin.

In some embodiments, generating the at least one signal generates a dehydrating signal, wherein generating the dehydrating signal includes performing an action selected from the group consisting of: generating a dry flow, generating a radio frequency signal, generating an optical signal, and generating a thermal heating signal.

In some embodiments, generating the at least one signal generates a stress signal, wherein generating the stress signal includes performing an action selected from the group consisting of: generating a dry flow, generating a radio frequency signal, generating a series of mechanical pulses, and generating a mechanical rotation.

In some embodiments, the method further includes applying a solution to the stratum corneum layer of the area of skin.

BRIEF DESCRIPTION OF THE DRAWINGS

The disclosed technique will be understood and appreciated more fully from the following detailed description taken in conjunction with the drawings in which:

FIGS. 2A-2C are schematic illustrations of a dermal conditioning device constructed and operative in accordance with an embodiment of the disclosed technique;

FIGS. 3D-3E are schematic illustrations of a sample of skin undergoing a non-ablative treatment by the dermal conditioning device of FIGS. 3A-3C, constructed and operative in accordance with a further embodiment of the disclosed technique;

FIG. 4F is a graph showing the temperature of the skin at a plurality of depths, in response to the application of the heating stage the dermal conditioning device of FIG. 2A in general, and the dermal conditioning device of FIG. 3A, in particular, constructed and operative in accordance with a further embodiment of the disclosed technique;

FIG. 4G shows a temperature gradient of the skin at various depths during the heating stage by the dermal condition device of FIG. 3A for a pulse duration of 8 ms, constructed and operative in accordance with another embodiment of the disclosed technique;

FIG. 4H is an illustration of an area of skin after undergoing an ablative treatment in accordance with prior art methods;

FIG. 4I is an illustration of an area of skin after undergoing the non-ablative treatment by the dermal conditioning device of FIG. 2A, constructed and operative in accordance with another embodiment of the disclosed technique;

FIGS. 6A-6B are schematic illustrations of a dermal conditioning device of the disclosed technique that produces heat using an RF emitter, constructed and operative in accordance with another embodiment of the disclosed technique.

DETAILED DESCRIPTION OF THE EMBODIMENTS

Figure 1A:
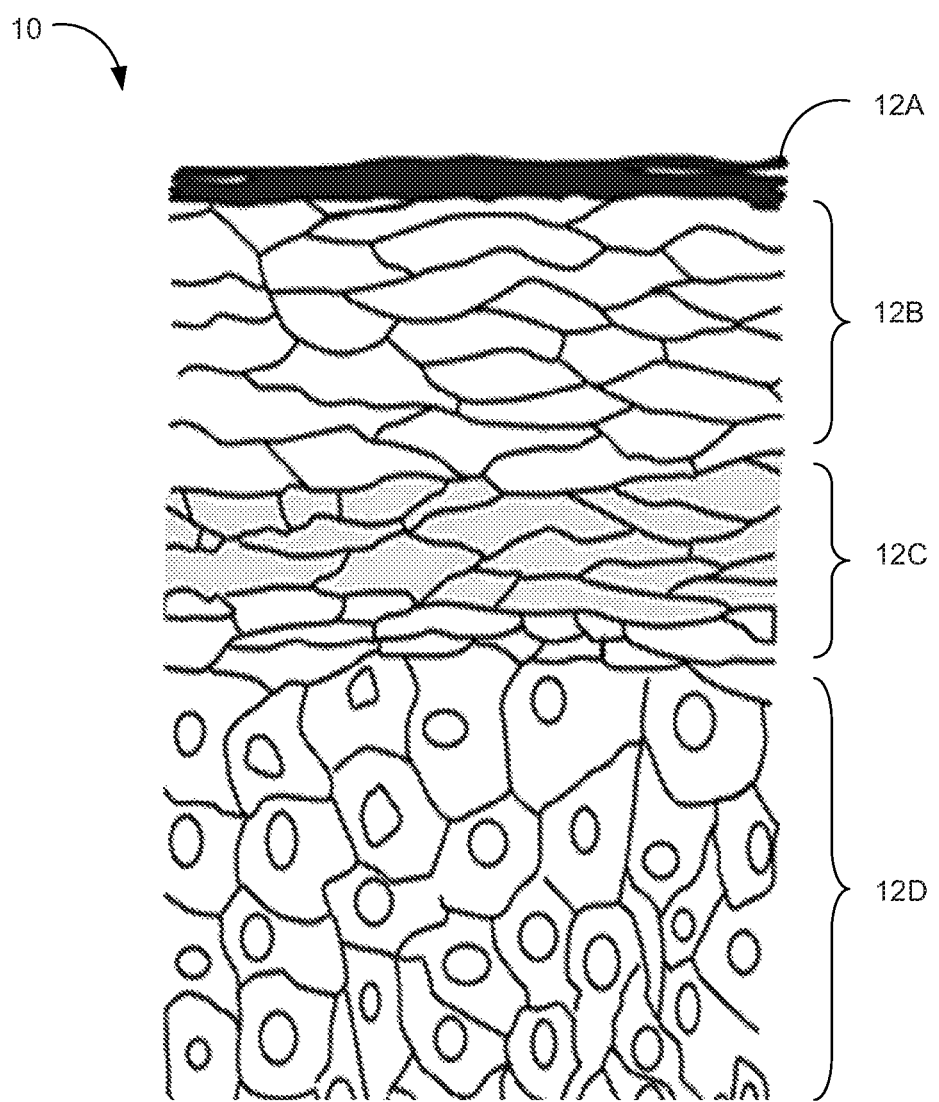
FIG. 1A is a schematic illustration of a cross section of a sample of epidermis, as is known in the prior art.

The disclosed technique overcomes the disadvantages of the prior art by providing a novel system, device and method for improving the absorption capability of an area of skin for intradermal delivery of substances using a non-invasive and non-ablative process. The stratum corneum layer of the skin is capable of absorbing up to three times its weight in water and is pliable and flexible when hydrated, however when the water content drops sufficiently, the stratum corneum becomes brittle and is prone to cracking. This property is true of both humans and animals. The disclosed technique utilizes this property to condition the skin for absorbing a solution or substance for cosmetic or medical treatment while maintaining the cellular integrity and viability of the skin tissue, preserving the penetration barrier function of the skin prior to treatment. According to the disclosed technique, the stratum corneum is dehydrated sufficiently such that it becomes brittle. A stress (i.e., force per cross-sectional area) is then applied to the brittle stratum corneum, which causes a strain on the stratum corneum resulting in a deformation. The strain causes the formation of a plurality of fissures in the stratum corneum while not ablating it. The fissures formed in the skin provide access channels to the deeper skin tissue layers, allowing these layers to absorb a hydrophilic, lipophilic or hydrophobic solution. Additionally, the fissures formed in the upper skin layers enable water to evaporate from the deeper skin layers in response to the continued application of heat to the external surface of the skin, i.e. the epidermis layer of the skin is dehydrated as well as part of the dermis layer, beneath the epidermis layer. The dehydration of the deeper skin layers causes the cells therein to be particularly receptive to absorbing hydrophilic and lipophilic solutions. The conditioning of the stratum corneum includes a heating stage and a stress-applying stage that does not penetrate the skin, and it thus non-invasive. The heating stage causes dehydration of the skin, and the stress-applying stage causes a strain on the skin, resulting in a deformation of the surface of the skin. The dehydration stage affects the stratum corneum layer as well as the deeper skin layers, whereas the strain-applying stage affects only the stratum corneum layer. The combination of first dehydrating and then applying stress causes the stratum corneum of the epidermal layer of the skin to become brittle and fissure without inducing trauma. The fissures in the stratum corneum form delivery channels from the external surface of the skin to the dehydrated but still viable cells residing below. This allows a solution, substance, drug, ointment and the like, applied to the skin's outer surface, to reach the deeper layers where it is absorbed. The dehydrating and stress-applying stages are applied externally to the skin in a precisely controlled manner that avoids penetration of the skin. The stress is applied to cause just a sufficient amount of strain on the surface of the skin to cause the formation of fissures without inducing trauma. By avoiding the inducement of trauma to the skin, the disclosed technique prevents a subsequent trigger of an inflammatory immune reaction, which would be detrimental to the absorption capability of the deeper skin layers. Thus, in contrast to conventional prior art techniques, the disclosed non-ablative technique results is in minimal coagulation or denaturation of the skin cells. The dehydrating stage and the non-invasive, strain-applying stage may be applied sequentially, in tandem or as a combination thereof.

The disclosed technique dehydrates the stratum corneum to less than 10% water content, leaving it brittle and prone to cracking and dehydrates the deeper layers, such as the stratum granulosum (the next layer below the stratum corneum) to less than 70% water content, increasing its absorption capability. Additionally, the disclosed technique applies a strain to the surface of the brittle stratum corneum layer, causing cracks to form. In this manner, thermal damage to the living cells in the deeper layers is prevented, maintaining their viability. Subsequently, the viable cells can absorb and react to a hydrophobic, lipophilic or hydrophilic solution delivered via the fissures. It is noted that the term "solution" in reference to intradermal delivery is used throughout the description to refer to medications, drugs, vaccines, ointments, creams, viscous substances and the like which can be administered through the skin. It is also noted that the term "skin" used throughout the description can apply to human skin as well as animal skin.

Figure 2A:
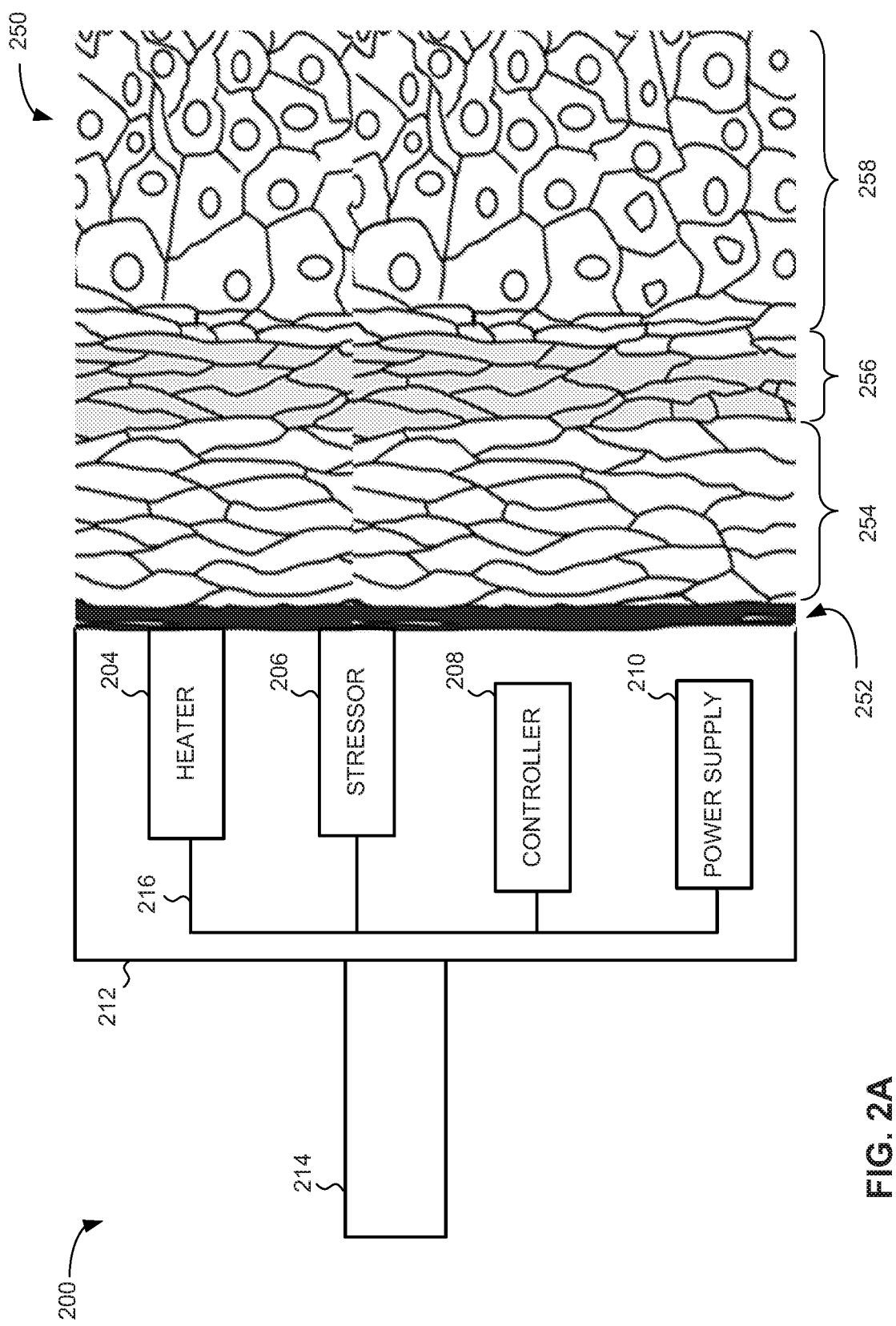
Figure 2B:
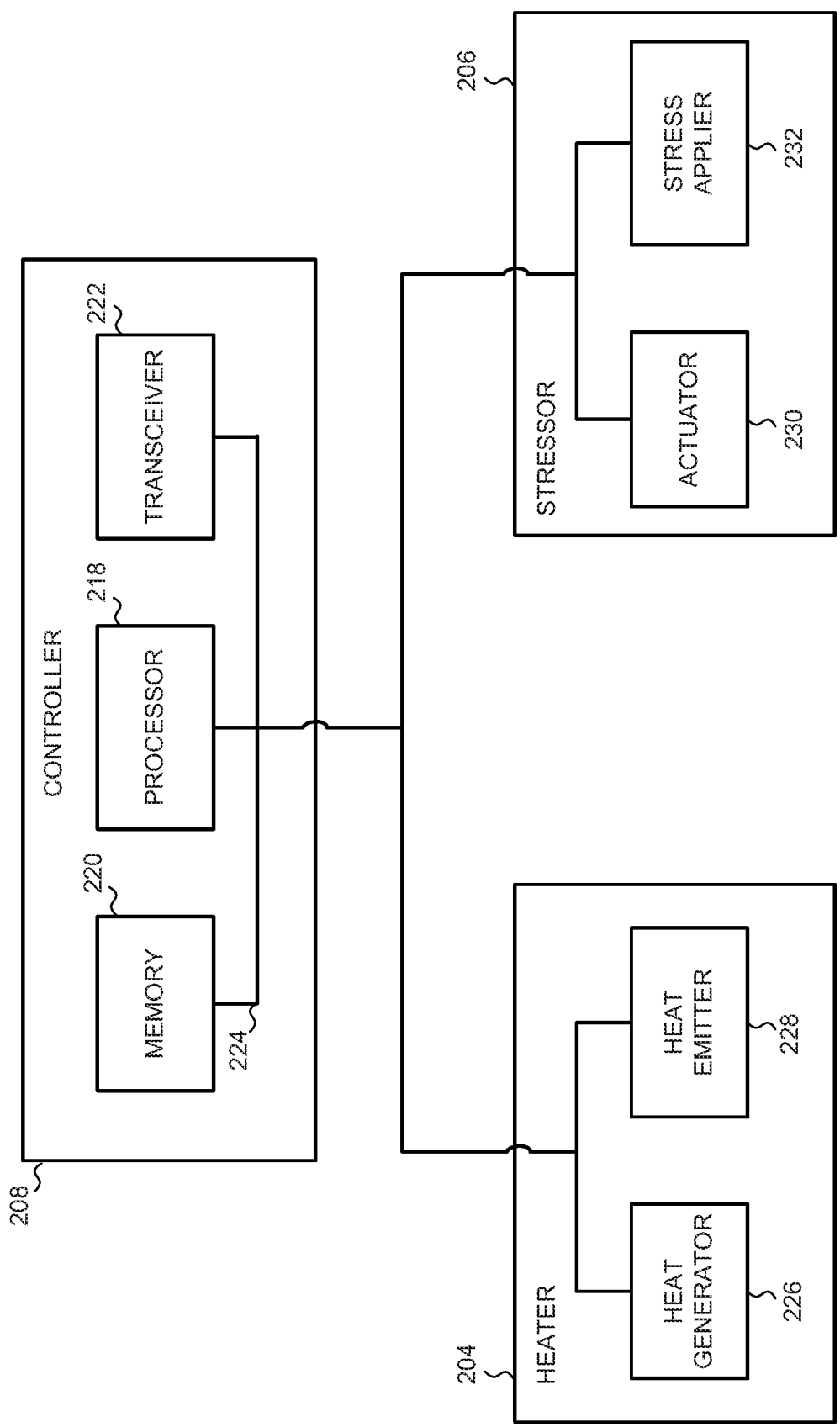

Reference is now made to FIGS. 2A-2B, which are schematic illustrations of the dermal conditioning device, generally referenced 200, constructed and operative in accordance with an embodiment of the disclosed technique. With reference to FIG. 2A, dermal conditioning device 200 is shown positioned in proximity to an area of skin 250. The layers of area of skin 250 are indicated as a stratum corneum layer 252, a stratum granulosum 254, a stratum spinosum 256 and a stratum basale 258. Stratum granulosum 254, stratum spinosum 256 and stratum basale 258 can collectively be referred to as deeper skin layers. FIG. 2A shows area of skin 250 prior to conditioning by dermal conditioning device 200, with stratum corneum layer 252 fully intact.

Dermal conditioning device 200 includes a heater 204, a stressor 206, a controller 208, and a power supply 210, all enclosed within a housing 212. Attached to housing 212 is a handle 214. Heater 204, stressor 206, controller 208 and power supply 210 are each electrically coupled to each other via a communications bus 216 that transfers data therebetween, using known techniques, including any of wired, optical fiber, and software (e.g. communications protocols) channels. Communications bus 216 may transfer data serially, in parallel or in a combination thereof. Heater 204 generates heat for dehydrating area of skin 250, in accordance with one or more heat control parameters as determined by controller 208. Heater 204 is thermally coupled to the distal end of dermal conditioning device 200 such that heat produced by heater 204 is delivered to area of skin 250 when positioned in sufficient proximity to the distal end of dermal conditioning device 200. The delivered heat causes water to evaporate from area of skin 250. Stressor 206 generates a stress for applying to area of skin 250, in accordance with one or more stress control parameters as determined by controller 208. The stress may be a mechanical stress, pressure exerted by air flow, and the like. Stressor 206 is coupled to the distal end of dermal conditioning device 200 such that the stress produced by stressor 206 is applied to area of skin 250 when positioned in sufficient proximity to the distal end of dermal conditioning device 200. The applied stress produces a strain on area of skin 250, resulting in the formation of a plurality of fissures.

As illustrated in FIG. 2A, prior to conditioning skin 250 by dermal conditioning device 200, stratum corneum layer 252 of the area of skin 250 is smooth and fully intact, having no significant fissures. In this state, stratum corneum layer 252 poses a barrier between deeper skin layers 254, 256, and 258 and the external surface of stratum corneum layer 252 facing the distal end of dermal conditioning device 200. Thus, stratum corneum layer 252 prevents the viable cells within deeper skin layers 254, 256, and 258 from absorbing an externally applied solution.

Reference is now made to FIG. 2B which is a schematic block diagram of controller 208, heater 204, and stressor 206 of FIG. 2A, constructed and operative in accordance with an embodiment of the disclosed technique. Controller 208 includes at least one processor 218, a memory 220, a transceiver 222, and a communications bus 224. Processor 218, memory 220, and transceiver 222 are electrically coupled to each other via communications bus 224. Communications bus 224 transfers data using known techniques, including any of wired, optical fiber, and software (e.g. communications protocols) channels. Communications bus 224 may transfer data serially, in parallel, or in a combination thereof. Transceiver 222 receives data via any known communications means, wired, wireless or both, such as through infrared technology, Bluetooth® technology, Ethernet technology and the like. The data may include one or more program code instructions, one or more parameters for controlling the operation of dermal conditioning device 200, and the like. Memory 220 is a computer readable media operative to store the one or more program code instructions, data, and operational parameters. Processor 218 applies the parameters when executing the one or more program code instructions to control the operation of dermal conditioning device 200, such as to control the operation of heater 204 and stressor 206 of FIG. 2A.

Controller 208 controls the operation of heater 204 and stressor 206 to apply the respective heat and strain to area of skin 250 either sequentially, simultaneously or a combination thereof. For example, controller 208 may first control the implementation of the dehydrating stage by heater 204 and then control the implementation of the stress-applying and strain-producing stage by stressor 206. In another embodiment, controller 208 may synchronize the operation of heater 204 and stressor 206 such that the dehydrating stage and stress-applying and strain-producing stage are implemented simultaneously.

Heater 204 includes a heat generator 224 and a heat emitter 226. Heat generator 224 is electrically coupled to controller 208 and power supply 210 (FIG. 2A). Heat emitter 226 is thermally coupled to heat generator 224 and to the distal end of dermal conditioning device 200 (FIG. 2A). Heat generator 224 generates heat in accordance with one or more heat control parameters, such as temperature (in degrees Celsius—° C.), wavelength (in nanometers—nm), energy level (in Joules—J), timing (in seconds) and the like. Controller 208 controls the operation of heat generator 224 in accordance with the heat control parameters. Heat emitter 226 emits the heat generated by heat generator 224 from the distal end of dermal conditioning device 200 onto area of skin 250, when area of skin 250 is positioned in proximity to the distal end of dermal conditioning device 200. Controller 208 controls the generation of heat by heat generator 224, and the emission of heat by heat emitter 226 to cause the dehydration of area of skin 250, such that the water content of stratum corneum layer 252 is less than 10% and the water content of stratum granulosum 254 is less than 70%. For example, controller 208 controls any of the timing, frequency, temperature, and intensity of the heat emitted by heat emitter 226. Controller 208 may receive feedback regarding the state of area of skin 250 from one or more sensors (not shown), and adjust the generation of heat by heat generator 224, and the emission of heat by heat emitter 226, accordingly.

In accordance with the disclosed technique, the following formulae are used to determine the parameters for operating heater 204. For a constant heat capacity, the amount of energy required to evaporate water may be calculated as:

$$\text{Energy} = (\text{mass}) \times (\text{temperature difference}) \times (\text{specific heat capacity}) \quad (1)$$

Even though live skin tissue does not have a constant heat capacity, over fairly narrow temperature ranges below 100° C. the variations in the heat capacity for skin tissue are fairly small and errors resulting from assuming a constant heat capacity are correspondingly small. For example, at atmospheric pressure, the specific heat capacity at constant pressure changes from 4.183 kJ/(kg·K) at 20° C. to 4.194 kJ/(kg·K) at 80° C., a change of only 0.3%. For other substances, such as superheated water, the variation in heat capacity with respect to temperature and pressure may be significant. At 350° C. (200 bar) the heat capacity is 8.138 kJ/(kg·K), nearly twice the heat capacity at 20° C. at the same pressure. The amount of heat required to evaporate water from live skin tissue can thus be calculated as the sum of the sensible heat ($Q_{sh}$) and the latent heat ($Q_{lh}$). Sensible heat in the context of the disclosed technique relates to the heat required to heat a tissue such that its surface temperature (usually 32° C.) is approximately 100° C. Latent heat is the heat required to change the state of heated water from liquid to vapor. Therefore the required heat, $Q_{Th}$, is given by the sum of the sensible heat and the latent heat as follows:

$$Q_{Th} = Q_{sh} + Q_{lh} \quad (2)$$

The sensible heat is calculated as the specific heat capacity of water, multiplied by the temperature change. The latent heat is calculated as the specific latent heat for water multiplied by the amount of water, measured as the mass of the water. Thus the required heat may be rewritten as:

$$Q_{Th} = C_m(T_2 - T_1) + mL \quad (3)$$

where L is the specific latent heat (for water this is 2264.76 kJ/(kg·K)), m is the mass (kg), $C_m$ is the specific heat capacity of water (4.2 kJ/(kg·K)), $T_2$ is the final temperature (° C.) of the skin and $T_T$ is the initial temperature (° C.) of the skin. Direct heat transfer (flow) from the distal end of dermal conditioning device 200 to the different layers of skin 250 may be determined by the following general equation.

$$\text{heat flow} = \frac{\text{Thermal potential difference}}{\text{Thermal resistance}} \quad (4)$$

More specifically, the thermal potential difference is given by the temperature differential, $T_i - T_j$, multiplied by the heat conductivity, $k_i$ and the thermal conductive area, A, and the thermal resistance is given by the thickness of the skin. Thus the direct heat transfer is determined by the following more specific equation:

$$q = -k_a A \frac{T_2 - T_1}{\Delta x_a} = -k_b A \frac{T_3 - T_2}{\Delta x_b} \quad (5)$$

where q is the heat flow, $T_i - T_{i-1}$ is the temperature difference within each skin layer, $\Delta x_a$, $\Delta x_b$ are the thicknesses for skin layers a, b, A is the thermal conductivity area of the skin, and $k_a$, $k_b$ are the heat conductivity for skin layers a, b, respectively.

The amount of heat absorbed by area of skin 250 is a function of the distance between heat emitter 228, positioned at the distal end of dermal conditioning device 200, and the thermal properties of skin 250. Since skin 250 is considerably large as compared to the distal tip of dermal conditioning device 200, the distal tip of dermal conditioning device 200 may be analyzed as a lumped mass. In a lumped mass the interior temperature remains essentially uniform throughout the heat transfer process and the temperature (T) can be taken to be a function of just time (t), thus giving T(t). The heat transfer for a lumped mass model is the heat transferred into area of skin 250 over a time interval dt, which equals to the increase in the energy of area of skin 250 during the time interval dt and can be expressed mathematically as the product of the heat transfer coefficient (h) over the contact area ($A_s$) of dermal conditioning device 200 with area of skin 250, multiplied by the temperature difference ($T_\infty - T$) over time period dl. This is equivalent to the mass (m) of the treated area of skin 250 multiplied by the specific heat c, of skin 250 and can be expressed as the following formula:

$$hA_S(T_\infty - T)dt = mc_p dT \quad (6)$$

where h is the heat transfer coefficient (W/(m²·K)), $A_s$ is the contact area of dermal conditioning device 200 with the treated area of skin 250, $T_\infty$ is the final temperature of area of skin 250 (° C.), T is the initial temperature of area of skin 250 (° C.), m is the mass (kg) of the treated area of skin 250 and $c_p$ is the specific heat of area of skin 250 (Kg·m²/(K·s²)).

Noting that m=ρV with ρ being the density of area of skin 250 (kg/m³), V being the volume (m³) of the treated area of skin 250, equation (5) may be rewritten as:

$$\frac{d(T - T_\infty)}{T - T_\infty} = \frac{hA_s}{\rho V c_p} dt \quad (7)$$

which can be solved, as follows:

$$\frac{T(t) - T_\infty}{T_i - T_\infty} = e^{-ibt} \quad (8)$$

where $$b = \frac{hA_s}{\rho V c_p} \quad (9)$$

Heat generator 226 may be implemented using any known technique for generating heat, as per the following examples:

Heat generator 226 may be a mechanical heat generator that heats via friction;

Heat generator 226 may be a heat generating element that is thermally coupled to a heat conducting element forming heat emitter 228, disposed at the distal end of dermal conditioning device 200;

Heat generator 226 may be a heat generating element coupled to an air pressurizer that is fluidly coupled to the distal end of dermal conditioning device 200 via multiple air channels forming heat emitter 228;

Heat generator 226 may be an infrared (herein IR) or near IR laser emitter optically coupled to heat emitter 228, configured as a plurality of fiber optic channels disposed at the distal end of dermal conditioning device 200; and Heat generator 226 may be an RF signal emitter electrically coupled to heat emitter 228, configured to channel the RF signal from the distal end of dermal conditioning device 200.

Stressor 206 includes an actuator 230 and a stress applier 232. Actuator 230 and stress applier 232 are coupled to each other such that a force actuated by actuator 230 is conveyed by stress applier 232 onto area of skin 250 when area of skin 250 is positioned in sufficient proximity to the distal end of dermal conditioning device 200. For example, actuator 230 may be mechanically coupled, electrically coupled, or fluidly coupled to stress conveyor 232. Exemplary embodiments are described in greater detail below in FIG. 5A-5E, however these examples are not intended to be limiting. Actuator 230 is electrically coupled to controller 208 and power supply 210 (FIG. 2A). Actuator 230 generates a stress in accordance with one or more stress control parameters, such as force (in Newtons—N), energy level (in Joules—J), frequency (in hertz—Hz), phase (in seconds), timing (in seconds) and the like. Actuator 230 may be any known stress actuator, such as a linear motor, a piezoelectric element, an RF emitter and the like, embodiments of which are described in greater detail below in FIGS. 6A-6B. Controller 208 controls the operation of actuator 230 in accordance with the stress control parameters mentioned above. Stress applier 232 conveys the stress generated by actuator 230 from the distal end of dermal conditioning device 200 onto area of skin 250. In response to the applied stress, a strain is produced on area of skin 250, resulting in the formation of a plurality of fissures.

With reference to FIG. 2C, dermal conditioning device 200 is shown in proximity to area of skin 250 after treatment by dermal condition device 200. Area of skin 250 is cracked, presenting a plurality of fissures 260 within dehydrated stratum corneum layer 252. Stratum corneum layer 252 is thinner after treatment by dermal condition device 200 than prior to treatment. Plurality of fissures 260 are caused by the strain produced on skin 250 as a result of the stress applied by stress applier 232. Each of plurality of fissures 260 provides a channel between the external surface of stratum corneum layer 252 and the deeper skin layers 254, 256, and 258. Notably, the cellular structure within stratum corneum layer 252 and deeper skin layers 254, 256, and 258 after the conditioning by dermal conditioning device 200 remains intact thereby exhibiting minimal trauma and coagulation. Conditioned thus, a solution (not shown) applied to the external surface of stratum corneum layer 252 can be transported via plurality of fissures 260 to deeper skin layers 254, 256, and 258, where the solution is absorbed by the cells residing therein.

Controller 208 controls the conditioning of skin 250 indicated in FIGS. 2A and 2C by controlling heater 204 to produce sufficient heat to dehydrate the area of skin 250 without causing thermal damage to any of the surface or deeper layers of area of skin 250. Heater 204 produces heat and applies the heat to the external surface of stratum corneum layer 252 of skin 250, thereby causing water stored therein to evaporate. In one embodiment, controller 208 controls the temperature, intensity and timing of the heat produced by heater 204 to cause evaporation from the epidermal layers of skin 250 (e.g. stratum corneum layer 252 and deeper skin layers 254, 256, and 258) until the respective water content of stratum corneum layer 252 is less than about 10% and until the respective water content of the extracellular matrix (herein abbreviated ECM) of stratum granulosum 200B is less than about 70%.

Controller 208 also controls stressor 206 to produce a stress that, when applied externally to stratum corneum layer 252, causes a strain on dehydrated stratum corneum layer 252 which is sufficient to crack dehydrated stratum corneum layer 252. Stressor 206 produces the stress and applies the stress to the external surface of stratum corneum layer 252 without is penetrating stratum corneum layer 252. The externally applied stress produces a strain on stratum corneum layer 252, causing the formation of plurality of fissures 260 in stratum corneum layer 252 without causing trauma to the layers of the epidermis of skin 250 to trigger an immune response. Thus the conditioning of skin 250 by dermal conditioning device 200 is non-invasive. The size and depth of plurality of fissures 260 may range from 20 to 300 microns. The ratio of fissured tissue to non-fissured tissue in the conditioned stratum corneum layer 252 may range between 1% and 30%. The ratio may be, for example, the ratio of the width of plurality of fissures 260 to the width of the intact regions of stratum corneum layer 252. Once conditioned, area of skin 250 is capable of absorbing a hydrophilic, lipophilic or hydrophobic solution applied to the external surface of fissured stratum corneum layer 252 into the viable cells within deeper skin layers 254, 256, and 258.

Figure 3A:
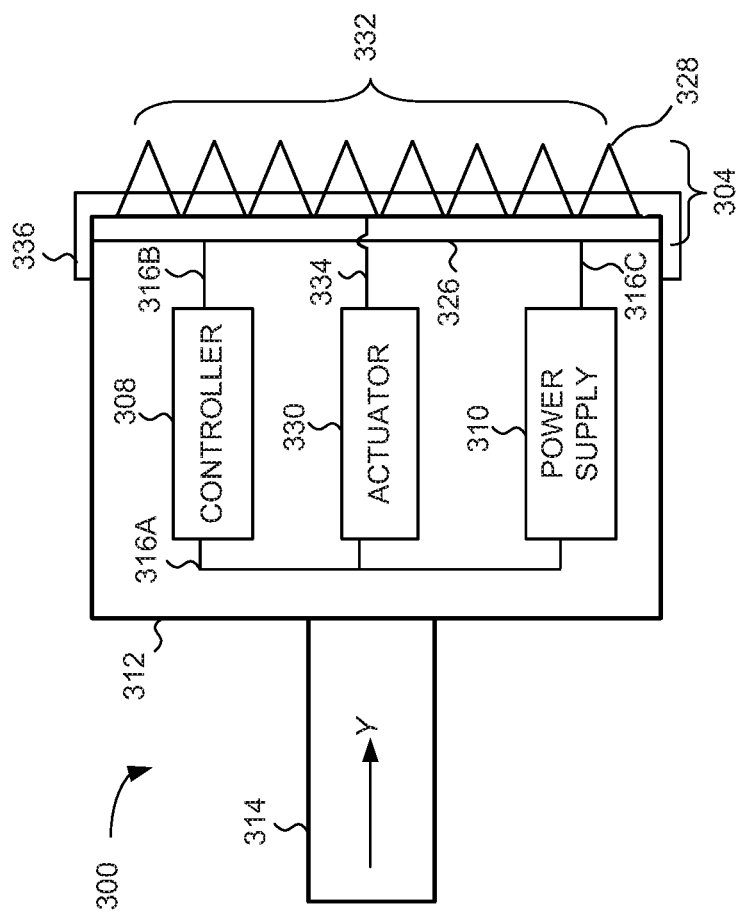
FIGS. 3A-3C, taken together, are a schematic illustration of an embodiment of the dermal conditioning device of the disclosed technique, constructed and operative in accordance with another embodiment of the disclosed technique.
Figure 3B:
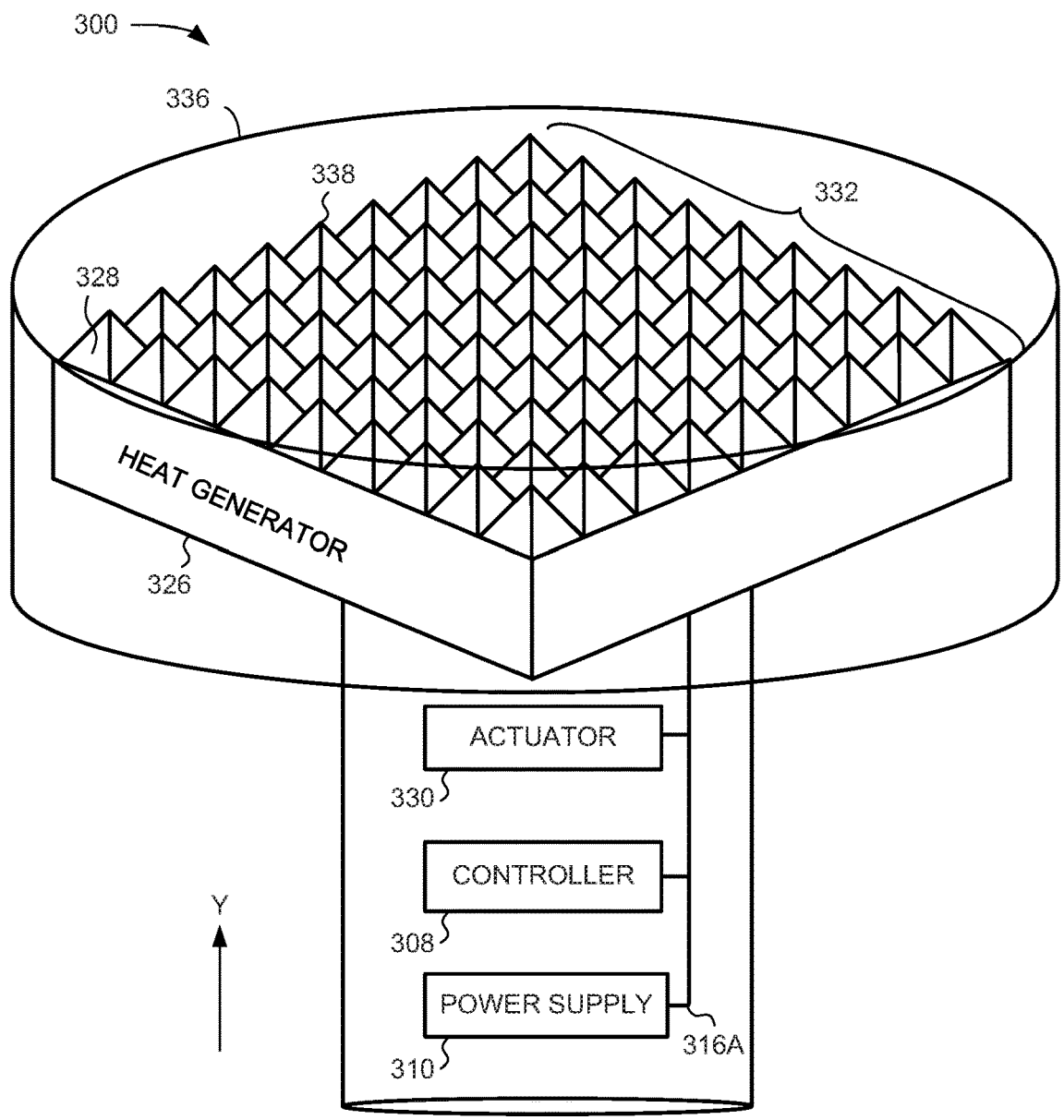
Figure 3C:
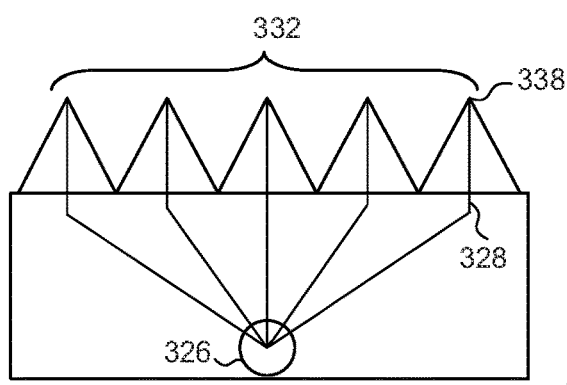

Reference is now made to FIGS. 3A-3C, which taken together, are a schematic illustration of an embodiment of the dermal conditioning device of the disclosed technique, generally referenced 300, constructed and operative in accordance with another embodiment of the disclosed technique. In the description that follows, dermal conditioning device 300 is understood to be operable to perform any of the procedures and/or functions described above with respect to dermal conditioning device 200 of FIGS. 2A-2C. With reference to FIG. 3A, dermal conditioning device 300 includes an actuator 306A, a controller 308, a power supply 310, communications buses 316A, 316B, and 316C, respectively, a heater 304 comprising a heat generator 326, shown as a thin element at the distal end of housing 312, and a heat emitter 328, shown as a heat conducting surface of a set of pyramid-shaped teeth at the distal end of dermal conditioning device 300, an actuator 330, a shaft 334, an actuator tip 332, and a distance gauge 336. Referring back to FIGS. 2A-28 while still referring to FIG. 3A, controller 308 corresponds to controller 208, power supply 310 corresponds to power supply 210, heater 304, heat generator 326 and heat emitter 328 correspond to heater 204, heat generator 226 and heat emitter 228, respectively, and actuator 330 and actuator tip 332 correspond to actuator 230 and stress applier 232, respectively.

Controller 308, actuator 330 and power supply 310 are electrically coupled via communications bus 316A. Controller 308 and power supply 310 are electrically coupled to heat generator 326 via communications buses 316B and 316C, respectively. Actuator 330 is mechanically coupled to actuator tip 332 via shaft 334. Actuator 330 is a linear motor operative to extend actuator tip 332 distally beyond distance gauge 336, and retract actuator tip 332 proximally behind distance gauge 336, in alignment with the longitudinal axis (Y) of dermal conditioning device 300, in accordance with the stress parameters. A more detailed description of actuator tip 332 is given below in FIG. 38.

Heater 304 is positioned at the distal end of dermal conditioning device 300, proximal to actuator tip 332. Heater 304 may be embodied using any suitable technique known in the art. For example, heat generator 326 of heater 304 may be a thermal heater such as a ceramic heater. Alternatively, heat generator 326 of heater 304 may be a laser light source. Heater 304 provides constant heat to the distal end of dermal conditioning device 300. In one embodiment, heat emitter 328 is a thermally conductive coating on actuator tip 332 such that heat emitter 328, together with actuator tip 332, form the distal end of dermal conditioning device 300. In this embodiment, heat generator 326 of heater 304 is thermally coupled to heat emitter 328, such as by using a spring (not shown) that presses heat generator 326 against the proximal base of heat emitter 328 and actuator tip 332 to ensure thermal matching, or alternatively by using a thermally conductive adhesive. Controller 308 controls the operation of heat generator 326 of heater 304 to maintain heat emitter 328 at a constant, effective temperature of approximately 400° C. during operation of dermal conditioning device 300.

With reference to FIG. 3B, dermal conditioning device 300 is shown from a perspective view. Actuator tip 332 is disposed at the distal end of dermal conditioning device 300. Actuator tip 332 includes an array of pyramid-shaped protrusions 338 that are aligned with the longitudinal axis of dermal conditioning device 300 (Y). The apexes of array of protrusions 338 form the distal end of dermal conditioning device 300. In one embodiment, actuator tip 332 includes a 9×9 grid of array of protrusions 338 covering an area of approximately 1 cm². The height of each one of array of protrusions 338 is approximately 1.25 mm. The surface area of the distal end of each protrusion 338 (for example, the surface area making contact with stratum corneum layer 252 (FIG. 2A)) is approximately $1.27\times104$ m². The spacing between the contact area of skin 250 and array of protrusions 338 of actuator tip 332 is sufficient, such that at any point in time, the temperature of any one of the contact areas of skin 250 with any one of array of protrusions 338 is thermally affected by only one of array of protrusions 338. Thus there are regions in between the areas of skin 250 in contact with array of protrusions 338 that remain at normal body temperature (i.e., 37° C.) throughout the treatment. Protrusions 338 may be made of a biocompatible, thermally conductive and thermally resilient material, such as gold-coated titanium, tungsten, tantalum or gold-coated stainless steel. In one embodiment of the disclosed technique, the thermal conductivity of protrusions 338 is less than the thermal conductivity of gold-coated copper to enable the heating of stratum corneum layer 252 (FIG. 2A) sufficiently to cause dehydration without causing ablation to viable tissue in area of skin 250 (FIG. 2A).

Distance gauge 336 of dermal conditioning device 300 is disposed at the respective distal end of dermal conditioning device 300. Distance gauge 336 encases array of protrusions 338 when dermal conditioning device 300 is not in use. During treatment, actuator 330 advances actuator tip 332 distally such that the distal end of protrusions 338 extend distally beyond distance gauge 336 by approximately 400 micrometers (herein abbreviated μm). Actuator 330 is operative to advance and retract actuator tip 332 in a harmonic pulsating motion in accordance with a predefined pulse duration and a predefined number of pulses per treatment, as controlled by controller 308, causing frictional heat in addition to a stress on stratum corneum layer 252. During contact with area of skin 250 by plurality of protrusions 338, the distal ends of array of protrusions 338 depress the surface of skin 250 without penetrating stratum corneum layer 252 (FIG. 2A). Plurality of protrusions 338 depress the surface of skin 250 in a non-invasive manner. The depression depth ranges between 0.1 millimeters (mm) to 1 mm, or from 0.05 to 1.2 mm, or from 0.2 mm to 0.8 mm, or from 0.3 mm to 0.7 mm, or from 0.4 to 0.6 mm. Thus, the conditioning of skin 250 by dermal conditioning device 300 is non-invasive. The contact time between protrusions 338 and skin 250 varies between 1-20 milliseconds (herein abbreviated ma) to allow sufficient heat transfer between array of protrusions 338 and skin 250 to cause substantial dehydration of skin 250 without substantial coagulation or burning. Typical pulse durations may range from 8 ms to 14 ms, or from 5 ms to 20 ms, or from 10 ms to 15 ms, or from 5 ms to 15 ms. In one embodiment, the distance of the harmonic pulsating motion of actuator tip 332 may range between 0.02 mm to 1.50 mm along the longitudinal axis of dermal conditioning device 300. The combination of the pulsating motion of actuator tip 332 with the heating by heater 304 causes area of skin 250 to heat rapidly, resulting in the evaporation of water from the surface of skin 250 as well as the fissuring of stratum corneum layer 252. Additionally, once stratum corneum layer 252 has fissured, the continual application of heat by heater 304 evaporates water from deeper skin layers 254, 256, and 258 (FIG. 2A).

Reference is now made to FIG. 3C, which is a schematic illustration of another implementation for the distal end of dermal conditioning device 300 of FIG. 3A. Heater 304 (FIG. 3A) includes a heat generator 326, positioned proximal to actuator tip 332. Heat generator 326 can be an optical emitter, such as an intensed pulse light (herein abbreviated IPL) light source, an IR or near IR light source, a solid state laser diode and the like, and heat emitter 328 includes multiple optical channels embedded within plurality of protrusions 338 that direct the light from heat generator 326 to the distal end of dermal conditioning device 300. Heat generator 326 may be implemented as a fractional $CO_2$ laser with a tissue penetration depth of 100 μm. Heat generator 326 may emit light at a wavelength of 2.94 μm, corresponding to the maximum absorption peak of water. Alternatively, the optical channels of heat emitter 328 may be positioned externally and adjacent to array of protrusions 338. Controller 308 (FIG. 3B) synchronizes the harmonic pulsating motion of actuator tip 332 with the emission of the light by heat generator 326. For example, controller 308 may control the emission of an IR laser by heat generator 326 such that the IR laser is emitted only when array of protrusions 338 makes physical contact with the area of skin 250. This may provide a safety measure to prevent the emission of the IR laser unless the device is in physical contact with the surface of area of skin 250. Alternatively, a sensor (not shown) may sense contact between actuator tip 332 and area of skin 250 and notify controller 308 to activate heat generator 326. The sensor may similarly notify controller 308 to deactivate heat generator 326 when no contact is detected between actuator tip 332 and area of skin 250.

Figure 3E:
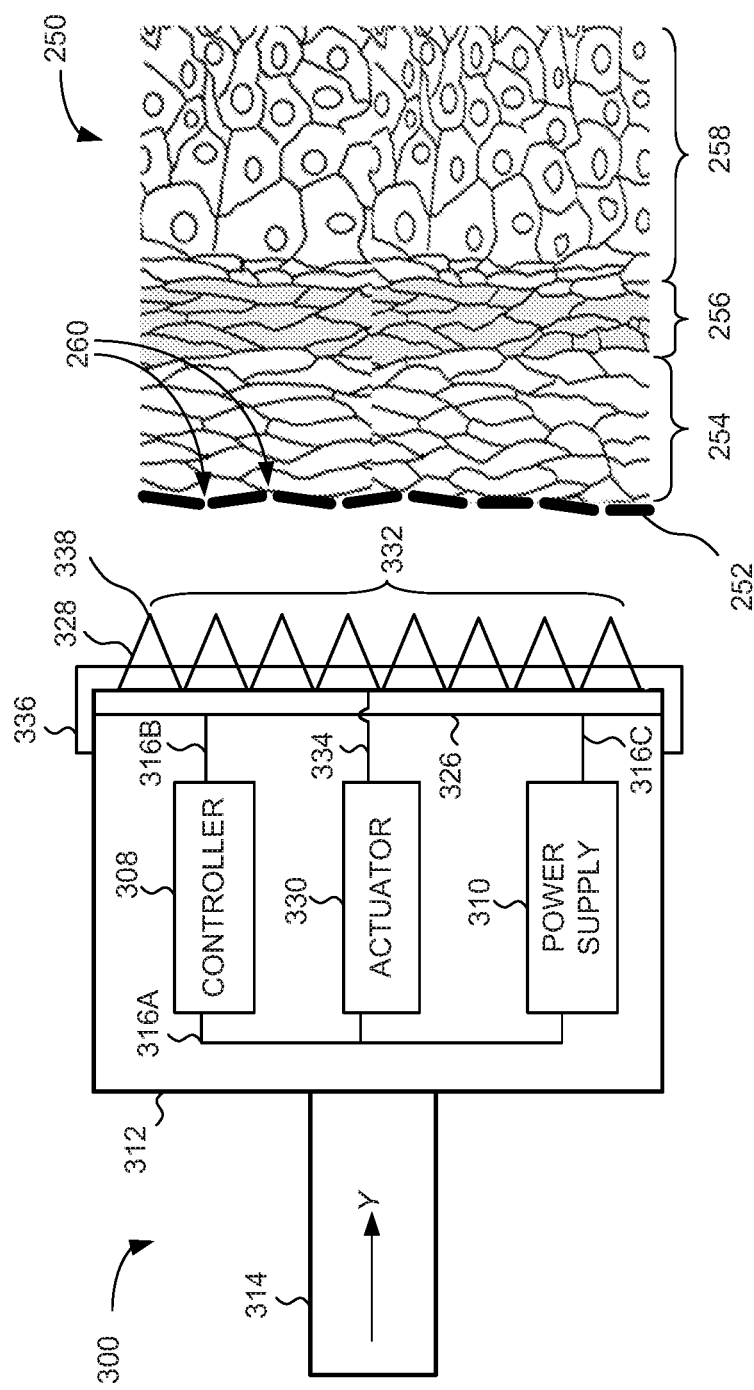

Reference is now made to FIGS. 3D-3E, which are schematic illustrations of a sample of skin undergoing a non-ablative treatment by dermal conditioning device of FIGS. 3A-3C, generally referenced 300, constructed and operative in accordance with a further embodiment of the disclosed technique. FIG. 3D shows an area of skin 250 prior to conditioning by a dermal conditioning device 300 and FIG. 3E shows area of skin 250 after conditioning by dermal conditioning device 300. With reference to FIG. 3D, the surface temperature of skin 250 is 37° C. (normal skin temperature) and skin 250 is fully hydrated. Stratum corneum layer 252 is intact serving as a barrier between the external surface of skin 250 and deeper skin layers 254, 256 and 258. With reference to FIG. 3E, skin 250 is dehydrated and stratum corneum layer 252 is thinner than in FIG. 3D. Stratum corneum layer 252 presents a plurality of fissures 260 that function as access channels to deeper skin layers 254, 256, and 256. Notably, the cells of deeper skin layers 254, 256, and 258 remain viable, allowing them to absorb a solution applied to the external, fissured surface of stratum corneum layer 252.

To achieve this conditioning of area of skin 250, controller 308 controls heat generator 326 to raise the temperature of the distal end of dermal conditioning device 300 to 400° C. Controller 308 sends a control signal to actuator 330 driving actuator tip 332 at pulses ranging from 8 ms to 14 ms. According to the disclosed technique, the duration of the stress pulses and the surface temperature of the distal end of dermal conditioning device 300 are computed in accordance with the following equation between the thermal wave penetration depth and the thermal properties of area of skin 250, analyzed using the lumped system analysis given above in equations (6)-(9):

$$\delta = 3.6\sqrt{\alpha t} = 3.6\sqrt{\frac{k}{\rho C_p} t} \tag{10}$$

where δ is the thermal wave penetration depth in meters, r is the thermal diffusivity in units of $m^2/s$, t is the time in seconds, k is the heat conductivity in units of W/m·° K, ρ is the density in units of $Kg/m^3$ and $C_p$ is the heat capacity at constant pressure in units of J/(Kg·° K).

Table 1 below gives heat conducting properties for area of skin 250.

TABLE 1

Heat conductivity respective of tissue density and heat capacity for different layers of area of skin 250

| | Conductivity (k) (W/m · ° K) | Density (ρ) (Kg/m³) | Heat Capacity ($C_p$) (J/Kg · ° K) |
|---|---|---|---|
| epidermis | 0.24 | 1200 | 3590 |
| dermis | 0.45 | 1200 | 3300 |
| Fat | 0.45 | 900 | 3300 |

Heat transfer from actuator tip 332 to area of skin 250 may be calculated according to the following equations:

$$\text{Heat}_{flux} = \iint (\text{total heat flux}) dA \tag{11}$$

Equation (11) describes the heat flux for each of array of protrusions 338 respective of area of skin 250. As per equation (11), the heat flux is calculated by integrating the heat flux per protrusion 338 over the contact surface area, A, of each of protrusions 338 with the surface skin 250. Thus the total amount of energy transferred to the area of skin 250 can be expressed by the following equation:

$$\text{Total}_Q = \int_0^t (\text{Heat}_{flux}) dt \tag{12}$$

This equation describes the amount of energy transferred to skin 250 from each of protrusions 338 for each pulse of duration t, and which is calculated by integrating the $\text{Heat}_{flux}$ per protrusion 338, calculated above in equation (11), over pulse duration t.

$$Q_{total_{tip}} = n \times \text{Total}_Q \tag{13}$$

This equation describes the amount of energy transferred to skin 250 from actuator tip 332 per pulse, calculated by multiplying the amount of energy transferred per protrusion 338 per pulse, by the number n of protrusions 338, which in the embodiment shown in FIG. 3B is 81. Plurality of protrusions 338 may be arranged according to need. For example, plurality of protrusions 338 may be arranged as a 4×6 array, a 12×12 array, a 10×10 array, a 15×15 array, a 10×15 array, and the like.

Table 2 below shows the amount of heat transferred from actuator tip 332 to skin 250, and the thermal penetration depth for a pulse duration of 8 ms and a pulse duration of 14 ms, respectively, as determined from a finite element analysis of dermal conditioning device 300 as described above in equations (6)-(9):

TABLE 2

Amount of heat transfer (J) to skin 250 by actuator tip 332 and thermal penetration depth (μm) of the applied heat for varying pulse durations (8 ms and 14 ms)

| Pulse Duration (ms) | Heat Transfer (J) | Thermal Penetration (μm) |
|---|---|---|
| 8 | 0.024 | 76 |
| 14 | 0.035 | 100 |

Figure 4A:
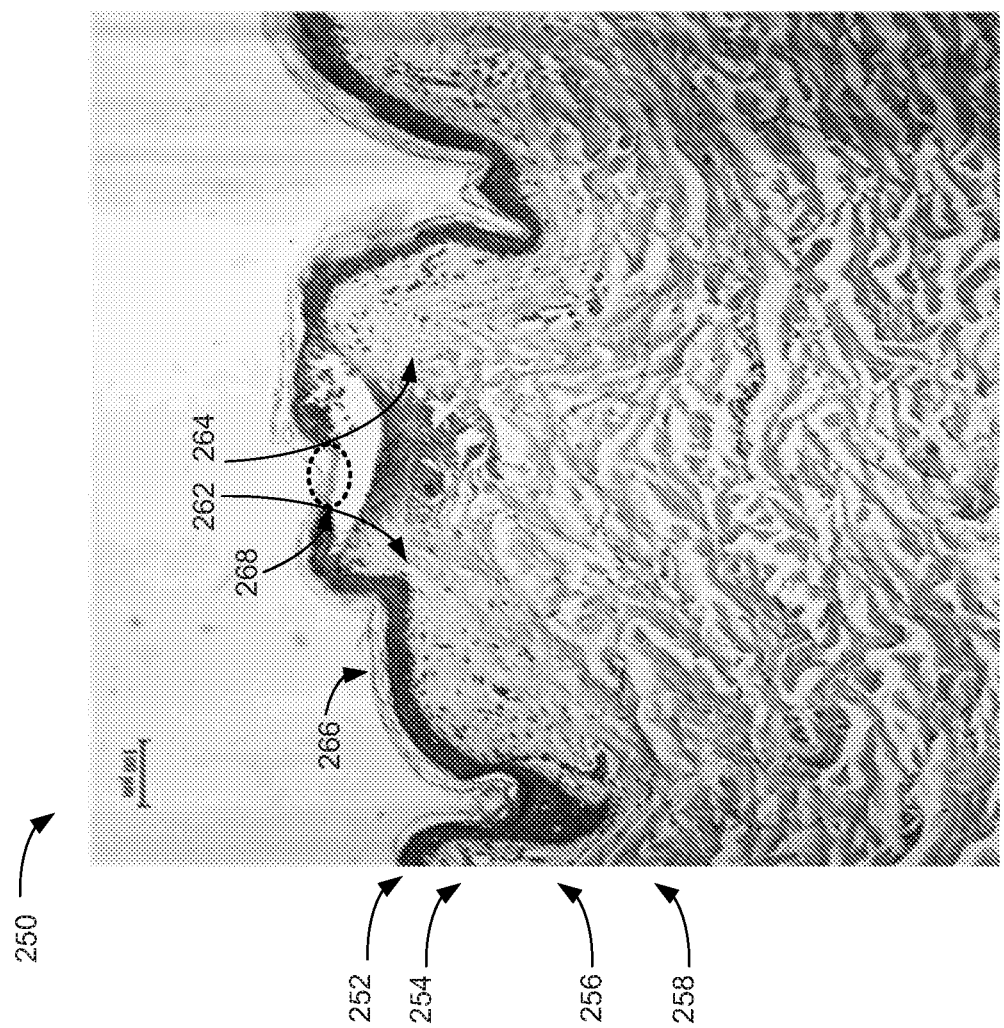
FIG. 4A is an image of an area of skin after undergoing the non-ablative treatment by the dermal conditioning device of FIGS. 3A-3C, constructed and operative in accordance with another embodiment of the disclosed technique.

Reference is now made to FIGS. 4A-4D, which illustrate the response of skin 250 to treatment by dermal conditioning device 300 of FIGS. 3A-3E at pulse durations of 8 ms and 14 ms. The numerical results were obtained from a finite element analysis of the skin, using equations (6)-(9) as given above. With reference to FIG. 4A, an image of an area of skin is shown after undergoing the non-ablative treatment by the dermal conditioning device of FIGS. 3A-3E, generally referenced 250, constructed and operative in accordance with another embodiment of the disclosed technique. Skin 250 is shown having an opening in stratum corneum layer 252, indicated by a dashed circle 268. Opening 268 leads to two fissures 262 and 264 through stratum corneum layer 252. Fissures 262 and 264 form free passage zones between the external surface of stratum corneum layer 252, is indicated as 266, and the internal deeper layers of skin 250, shown as stratum granulosum 254, stratum spinosum 256 and stratum basale 258. The cells within stratum granulosum 254, stratum spinosum 256, and stratum basale 258 are dehydrated while still retaining their viability and are thus receptive to absorbing a solution applied externally via fissures 262 and 264. Notably, there is minimal coagulation or denaturing within stratum granulosum 254, stratum spinosum 256, and stratum basale 258. Skin 250 was not mechanically perforated by protrusions 338 (FIG. 3B), rather fissures 262 and 264 were created by the combination of the dehydration and the non-invasive compression load/stress applied to stratum corneum layer 252 by dermal conditioning device 300 (FIGS. 3A-3E), and the resulting strain on stratum corneum layer 252 caused by this stress. Similarly, the effect of dermal conditioning device 300 on the deeper layers of skin 250 (i.e., deeper skin layers 254, 256, and 258) is to primarily evaporate water from the ECM while minimizing thermal damage to live tissue.

Figure 4B:
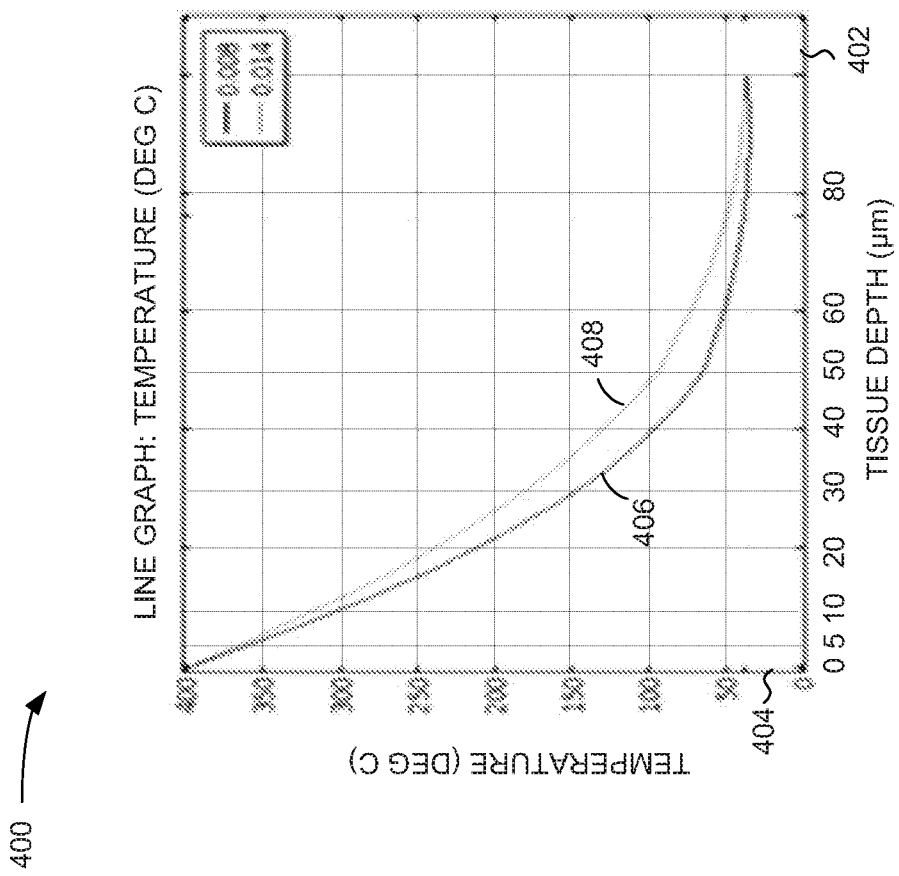
FIG. 4B is a graph illustrating the heat wave penetration depth for skin responsive to treatment by the dermal conditioning device of FIGS. 3A-3C, constructed and operative in accordance with a further embodiment of the disclosed technique.

With reference to FIG. 4B, a graph illustrating the heat wave penetration depth for skin responsive to treatment by dermal conditioning device of FIGS. 3A-3C is shown, generally referenced 400, constructed and operative in accordance with a further embodiment of the disclosed technique. Graph 400 includes a horizontal axis 402 showing tissue depth in micrometers and a vertical axis 404 showing temperature in degrees Celsius. A curve 406 depicts the heat wave penetration depth for skin 250 responsive to being treated by dermal conditioning device 300 (FIGS. 3A-3C) with a pulse duration of 8 ms whereas and a curve 408 depicts the heat wave penetration depth for skin 250 responsive to being treated by dermal conditioning device 300 with a pulse duration of 14 ms. With respect to curve 406 respective of an 8 ms pulse duration, at a depth of 0 μm, the temperature of skin 250 reaches 400° C., at a depth of 5 μm the temperature of skin 250 reaches 350° C., at a depth of 10 μm the temperature of skin 250 reaches 300° C., and at a depth of 30 μm the temperature of skin 250 reaches 150° C. With respect to curve 222 respective of a 14 ms pulse duration, at a depth of 0 μm, the temperature of skin 250 reaches 400° C., at a depth of 5 μm the temperature of skin 250 reaches 360° C., at a depth of 10 μm the temperature of skin 250 reaches 320° C. and at a depth of 30 μm the temperature of skin 250 reaches 180° C. As can be seen from curves 406 and 408, the most significant temperature increase occurs at the surface of skin 250, at a depth of 0 μm. The temperature of the deeper layers of skin 250, e.g. layers 254, 256, and 258 of FIGS. 3D-3E, decreases dramatically at a steep slope, tapering at about 50 μm, where the temperature decreases at a gentle slope. This characteristic prevents ablation and tissue damage at the deeper skin layers, maintaining the viability of these cells.

Figure 4C:
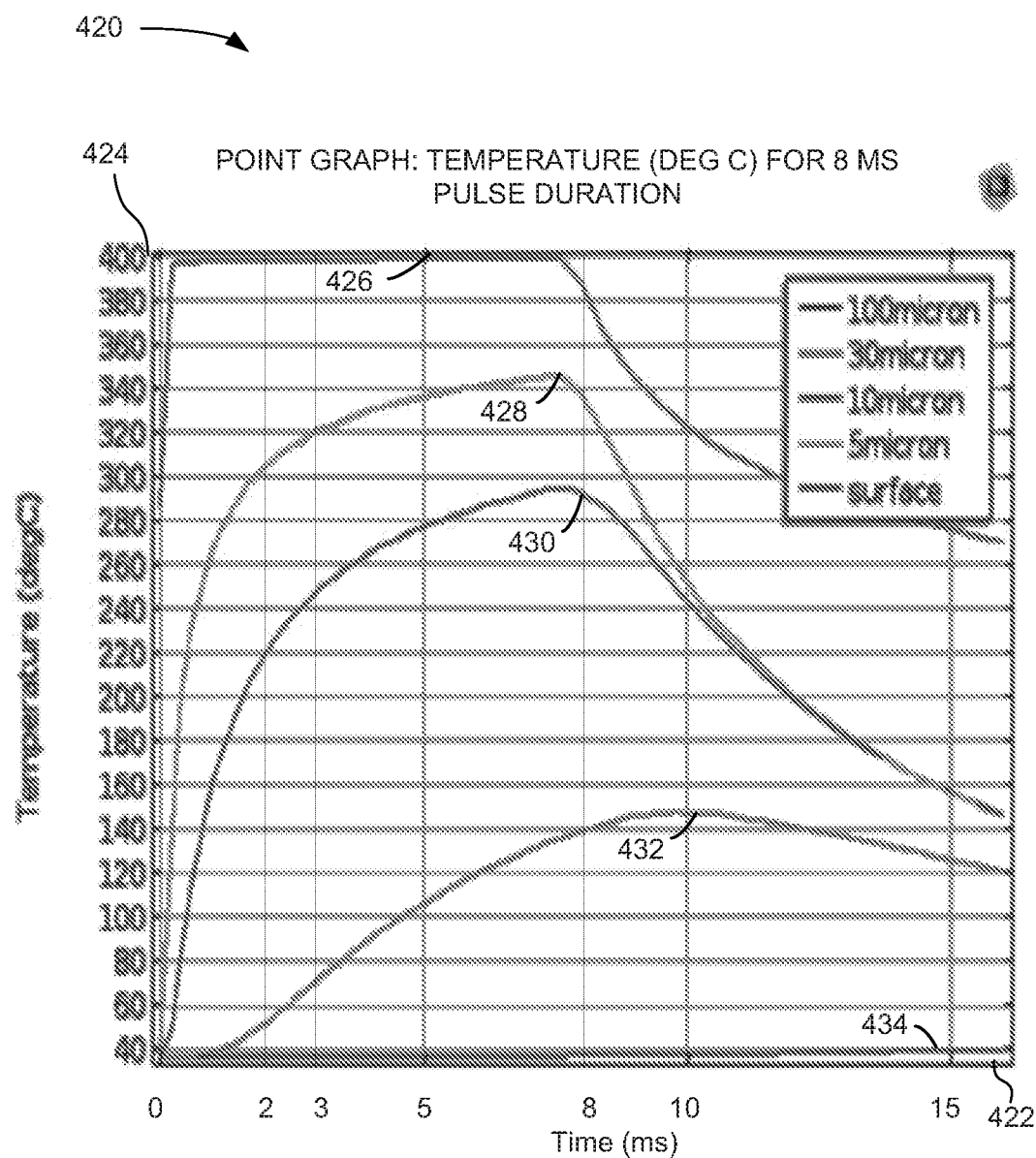
FIG. 4C is a graph showing the temperature of skin at varying skin depths over 15 ms after treatment by the dermal conditioning device of FIGS. 3A-3C for a pulse of duration 8 ms, constructed and operative in accordance with another embodiment of the disclosed technique.

Reference is now made to FIG. 4C, which is a graph showing the temperature of skin at varying skin depths over 15 ms after treatment by dermal conditioning device of FIGS. 3A-3C for a pulse of duration 8 ms, generally referenced 420, constructed and operative in accordance with another embodiment of the disclosed technique. Graph 420 includes a horizontal-axis 422 showing time in milliseconds and a vertical-axis 424 showing temperature in degrees Celsius. The topmost curve, referenced 426, illustrates the changes to the surface temperature of skin 250, in other words the external side of stratum corneum layer 252, over 15 ms on being treated to an 8 ms pulse by device 300. At the onset of the pulse, the surface temperature of skin 250 rises rapidly, reaching the peak temperature of 400° C. within 1 ms. The surface of stratum corneum layer 252 is maintained at a constant temperature of 400° C. for the 8 ms duration of the pulse, after which the temperature begins to drop, reaching 320° C. after 10 ms and approximately 260° C. after 15 ms.

The curve referenced 428 illustrates the changes to the temperature of skin 250 over 15 ms at a depth of 5 μm, corresponding to the middle region of stratum corneum layer 252, on being treated to an 8 ms pulse by dermal conditioning device 300. At the onset of the pulse, the temperature increases rapidly for the first 2 ms, reaching approximately 300° C., after which the temperature continues to increase at a slower rate, reaching a peak temperature of nearly 350° C. at 8 ms. After 8 ms, the temperature decreases fairly rapidly, falling to about 250° C. at 10 ms and continuing to decrease below 160° C. after 15 ms.

The curve referenced 430 illustrates the changes to the temperature of skin 250 over 15 ms at a depth of 10 μm, corresponding to the border between stratum corneum layer 252 and stratum granulosum 254, on being treated to an 8 ms pulse by dermal conditioning device 300. At the onset of the pulse, the temperature increases rapidly for the first 3 ms, reaching 260° C., after which the temperature continues to increase at a slower rate, reaching a peak temperature of nearly 300° C. at 8 ms. After 8 ms, the temperature decreases fairly rapidly, falling to about 240° C. at 10 ms and continuing to decrease below 160° C. after 15 ms. Curves 430 (10 μm) and 428 (5 μm) converge after about 12 ms. The curve referenced 432 illustrates the changes to the temperature of skin 250 over 15 ms at a depth of 30 μm, corresponding to just below stratum basale 258 (the border between the epidermis and dermis layers of the skin), on being treated to an 8 ms pulse by dermal conditioning device 300. At the onset of the pulse, the temperature increases almost linearly, reaching almost 150° C. after 8 ms. After 8 ms, the temperature decreases fairly linearly, but slower than the increase, reaching 120° C. after 15 ms.

The curve referenced 434 illustrates the changes to the temperature of tissue beneath skin 250 over 15 ms at a depth of 100 μm, on being treated to an 8 ms pulse by dermal conditioning device 300. At the onset of the pulse, the temperature of the deep tissue barely changes from normal body temperature of 37° C., reaching 40° C. after 15 ms.

As may be seen from graph 420, only the surface temperature of skin 250, represented by curve 426, is maintained at 400° C. throughout the duration of the pulse, allowing for significant dehydration and the formation of fissures. The temperature of the deeper skin layers 254 and 256, at depths of 5 μm and 10 μm respectively, represented by curves 428 and 430, rises somewhat allowing for dehydration without causing damage to the viable cells. However the temperature of the deep tissue, beneath 30 μm until 100 μm, represented by curves 432 and 434, respectively, rises only mildly, preventing damage to these areas.

Figure 4D:
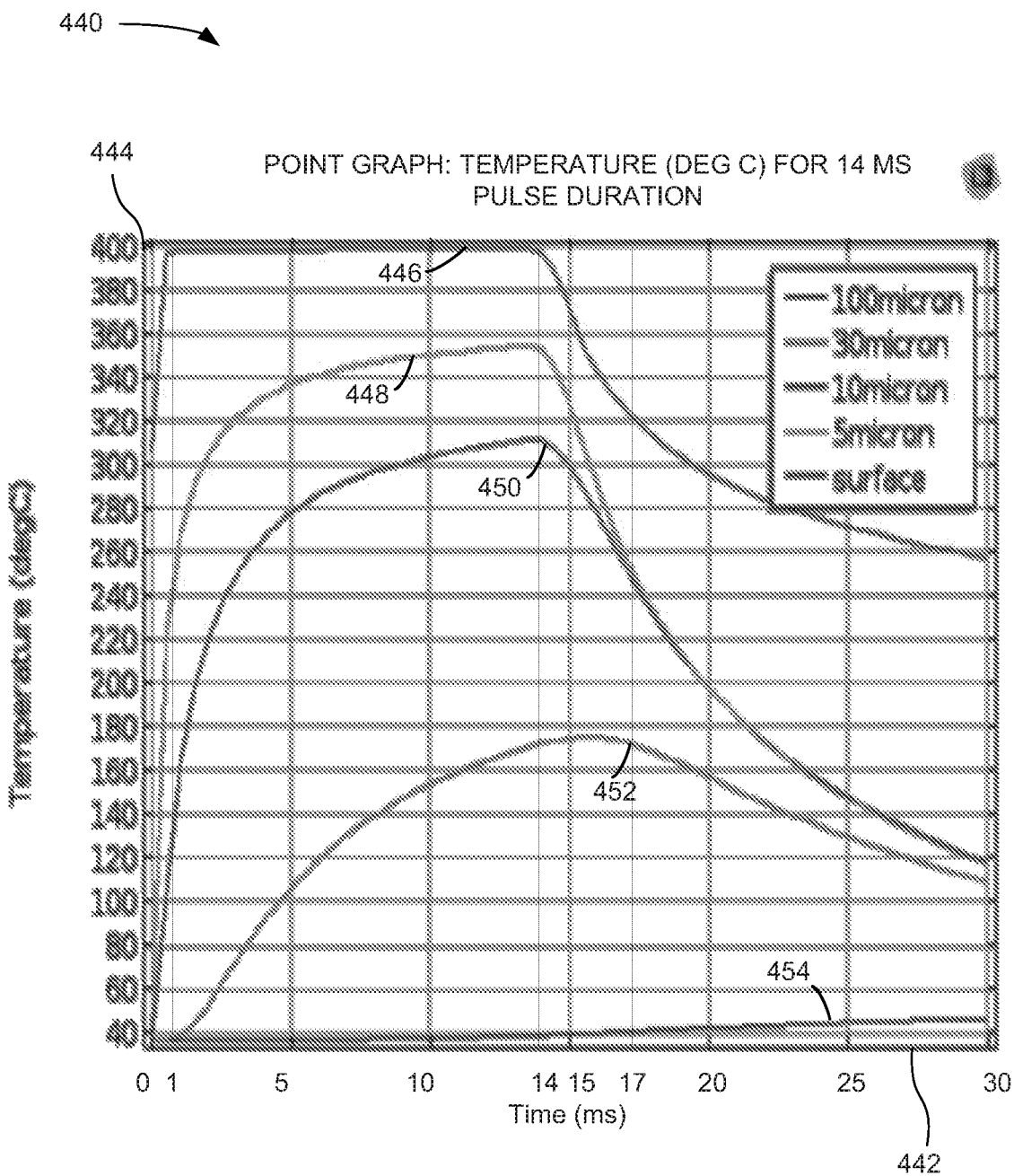
FIG. 4D is a graph showing the temperature of skin at varying skin depths over 30 ms after treatment by the dermal conditioning device of FIGS. 3A-3C for a pulse of duration 14 ms, constructed and operative in accordance with a further embodiment of the disclosed technique.

Reference is now made to FIG. 4D which is a graph showing the temperature of skin at varying skin depths over 30 me after treatment by the dermal conditioning device of FIGS. 3A-3C for a pulse of duration 14 ms, generally referenced 440, constructed and operative in accordance with a further embodiment of the disclosed technique. Graph 440 includes a horizontal-axis 442 showing time in milliseconds and a vertical-axis 444 showing temperature in degrees Celsius. The topmost curve, referenced 446 illustrates the changes to the surface temperature of skin 250, e.g. the external side of stratum corneum layer 252, over 30 ms on being treated to a 14 ms pulse by dermal conditioning device 300 (FIGS. 3A-3C). At the onset of the pulse, the surface temperature of skin 250 rises rapidly, reaching the peak temperature of 400° C. within 1 ms. The surface of stratum corneum layer 252 is maintained at a constant temperature of 400° C. for the 14 ms duration of the pulse, after which the temperature begins to drop, reaching 370° C. after 15 ms, and just below 260° C. after 30 ms.

The curve referenced 448 illustrates the changes to the temperature of skin 250 over 30 ms at a depth of 5 μm, corresponding to the middle region of stratum corneum layer 252, on being treated to a 14 ms pulse by dermal conditioning device 300. At the onset of the pulse, the temperature increases rapidly for the first 3 ms, reaching approximately 320° C., after which the temperature continues to increase at a slower rate, reaching a peak temperature of nearly 360° C. at 14 ms. After 14 ms, the temperature decreases fairly rapidly, falling to about 240° C. at 17 ms, and continuing to decrease to below 120° C. after 30 ms.

The curve referenced 450 illustrates the changes to the temperature of skin 250 over 30 ms at a depth of 10 μm, corresponding to the border between stratum corneum layer 252 and stratum granulosum 254, on being treated to a 14 ms pulse by dermal conditioning device 300. At the onset of the pulse, the temperature increases rapidly for the first 3 ms, reaching 260° C., after which the temperature continues to increase at a slower rate, reaching a peak temperature of approximately 310° C. at 17 ms. After 14 ms, the temperature decreases fairly rapidly, falling to about 240° C. at 17 ms, and continuing to decrease below 120° C. after 30 ms. The 10 μm curve 450 and the 5 μm curve 448 converge after about 17 m.

The curve referenced 452 illustrates the changes to the temperature of skin 250 over 30 ms at a depth of 30 μm, corresponding to just below stratum basale 258, on being treated to a 14 ms pulse by dermal conditioning device 300. At the onset of the pulse, the temperature increases more gradually throughout the duration of the pulse, reaching a peak temperature of nearly 180° C. at 14 ms, after which the temperature decreases gradually, falling to just below 110° C. at 30 ms.

The curve referenced 454 illustrates the changes to the temperature of tissue beneath skin 250 over 30 ms at a depth of 100 μm, on being treated to a 14 ms pulse by dermal conditioning device 300. At the onset of the pulse, the temperature of the deep tissue barely changes from normal body temperature of 37° C., reaching just under 45° C. after 30 ms.

As may be seen from graph 440, the temperature rise and decay patterns are similar as for graph 420 (FIG. 4C). Only the surface temperature of skin 250, represented by curve 446, is maintained at 400° C. throughout the duration of the pulse, allowing for significant dehydration and the formation of fissures on the stratum corneum. The temperature of the deeper skin layers 254 and 256, at depths of 5 μm and 10 μm respectively, represented by curves 448 and 450, rises somewhat allowing for partial dehydration without causing damage to the viable cells therein. However the temperature of the deep tissue, beneath 30 μm until 100 μm, represented by curves 452 and 454, respectively, rises only mildly, thereby preventing damage to these areas.

In general, the application of the heating stage by dermal condition device 300 (FIG. 3A), and more generally by dermal condition device 200 (FIG. 2A) on skin 250, causes the dehydration of stratum corneum layer 252 and deeper skin layers 254, 256, and 258. As a result of the dehydration, there is concentration gradient between a solution, subsequently introduced to the external surface of skin 250, and dehydrated stratum corneum layer 252 and deeper skin layers 254, 256, and 258. The concentration gradient is greater than any concentration gradient present in other areas of skin 250 that were not treated by dermal conditioning device 200. The concentration gradient caused by the conditioning of skin 250 by dermal conditioning device 200 aids in accelerating the absorption of the introduced solution through stratum corneum layer 252, into the viable cells residing in deeper skin layers 254, 256, and 258. Additionally, when stratum corneum layer 252 is dehydrated, the concentration gradient external to stratum corneum layer 252 of skin is substantial. For example the solution may have a water content ranging between 75% and 100%, or between 80% and 90%, or between 60% and 100%, and the water content of dehydrated stratum corneum layer 252 may range between 0% and 10%, or between 5% and 15%, or between 10% and 20%. By contrast, the concentration gradient internal to stratum corneum layer 252 is less substantial. For example, stratum granulosum layer 254 may be dehydrated to reach a water content of 70%, or 75%, or 65%, or 80%, corresponding to the heat penetration depth. The water content level of stratum granulosum layer 254 gradually decreases from this level as the distance from dehydrated stratum corneum layer 252 decreases, i.e. moving upwards through partially dehydrated stratum granulosum layer 254, transitioning through water content levels 50%, 40%, 30% and 20% to reach dehydrated stratum corneum layer 252 having a water content ranging from 0% to 10%, or from 5% to 15%. This difference between the concentration gradient external to skin 250 versus the concentration gradient internal to skin 250 may further accelerate the absorption of an externally applied solution.

Additionally, the total amount of heat energy applied to skin 250 by dermal condition device 300 (FIG. 3A), and more generally by dermal condition device 200 (FIG. 2A), during treatment is relatively small. The applied heat energy is a function of the physical dimensions and design of dermal conditioning device 200 in general. A heat transfer analysis describing the applied heat energy for the specific case of dermal condition device 300 (FIG. 3A) is described above in equations 11-13. The heat transfer analysis takes into account the size, shape, and material of actuator tip 332, and additionally of the method by which controller 308 controls the application of heat by heat emitter 328 in accordance with the heat parameters (e.g. pulses of 8 ms and 14 ms, heating actuator tip to 400° C., etc). However, such analysis is not intended to be limited to the embodiment of FIGS. 3A-3E. It is to be understood that a similar heat transfer analysis may be performed for each of the embodiments disclosed herein, in accordance with heat transfer analysis as is known in the art, to achieve the desired heat energy transfer to skin 250 that fissures stratum corneum layer 252 without causing excess coagulation.

Accordingly, the amount of coagulated tissue within skin 250 on being treated by dermal conditioning device 300 (FIG. 3A), and in general by dermal conditioning device 200 (FIG. 2A), is significantly reduced as compared to conventional techniques. This reduction in skin coagulation is evident by comparing skin 20 (FIG. 1A) and skin 30 (FIG. 18), having been treated by prior art techniques with skin

Figure 1C:
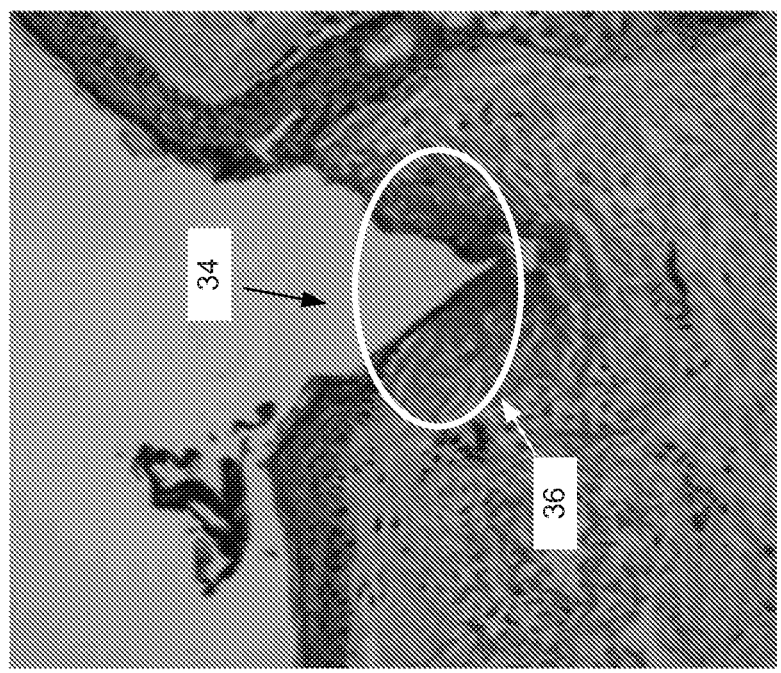
FIG. 1C is an image of a sample of skin having undergone an to ablative treatment using a radio frequency process, as is known in the prior art.
Figure 1B:
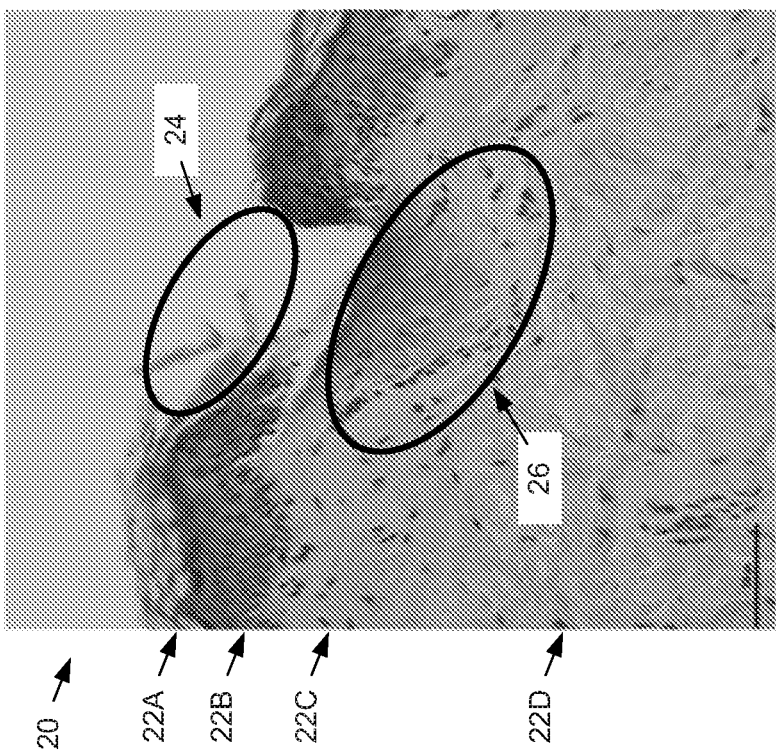
FIG. 1 is an image of a sample of skin having undergone an ablative laser treatment, as is known in the prior art.

250 (FIG. 4A), having been treated by dermal condition device 300 (FIG. 3A), and more generally by dermal condition device 200 (FIG. 2A). As may be seen by comparing these images, the coagulation present in skin 20 (FIG. 1A) and skin 30 (FIG. 1) is significantly greater than any coagulation present in skin 250 (FIG. 4A). This reduction in tissue coagulation reduces the barrier posed by such tissue coagulation, further enhancing the absorption capability by the viable cells of deeper skin layers 254, 256, and 258, to the introduced solution.

Figure 4E:
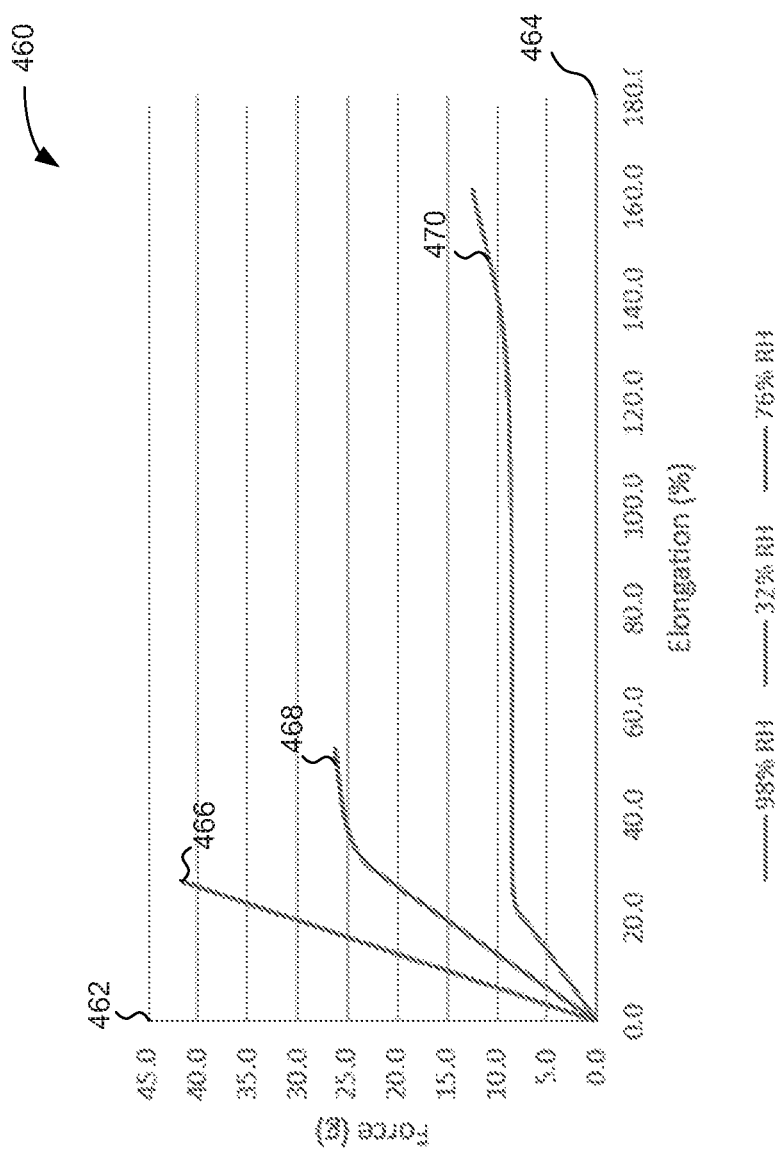
FIG. 4E is a graph illustrating the relationship between an applied stress and a corresponding elongation of a plurality of materials in response to the applied stress, constructed and operative with another embodiment of to the disclosed technique.

Reference is now made to FIG. 4E, which is a graph, generally referenced 460, illustrating the relationship between an applied stress and a corresponding elongation of a plurality of materials in response to the applied stress, constructed and operative with another embodiment of the disclosed technique. Each of the plurality of materials have a different relative humidity, and thus respond differently to the applied force. The applied stress is indicated on the vertical axis 462 and labelled "Force", as measured in grams (g). The elongation is indicated on the horizontal axis 464 and labelled "Elongation", as measured by the percentage (%) elongation respective of the initial length prior to applying the force.

Curve 466 shows the elongation properties for a brittle material having a relative humidity of 32%, such as described above with respect to stratum corneum layer 252 after applying the dehydration stage by any of dermal conditioning device 200 (FIG. 2A), and dermal conditioning device 300 (FIG. 2B). Accordingly, increasing the applied force until 40 g elongates this material by approximately 20%, causing it to thin, and making this material prone to breaking or cracking when additional force is applied. Curve 468 shows the elongation properties for a material undergoing rapid heating at low energy, reaching a relative humidity of 76%, such as described above with respect to stratum granulosum layer 254 (FIG. 4A) after applying the dehydration stage by any of dermal conditioning device 200 (FIG. 2A), and dermal conditioning device 300 (FIG. 3A). Increasing the applied force from 0 g to 23 g modestly elongates this material in a linear-like relationship. On increasing the applied force above 23 g, the material continues to elongate (e.g. stretches) considerably and does not crack. Curve 470 shows the elongation properties for a material having a relative humidity of 98%, such as deeper skin layers 256, and 258. Accordingly, such a material elongates considerably in response to the applied force, and does not crac.

Reference is now made to FIG. 4F which is a graph, generally referenced 471, showing the temperature of the skin at a plurality of depths, in response to the application of the heating stage by any of dermal conditioning device 200 (FIG. 2A) in general, and dermal conditioning device 300 (FIG. 3A) in particular, constructed and operative in accordance with a further embodiment of the disclosed technique. The applied heat is indicated on the vertical axis 472, labelled "Temperature" as measured in ° C., and the skin depth is indicated on the horizontal axis 474 labelled "skin depth", as measured in μm. Curve 476A shows the temperature of skin 250 at the surface corresponding to a depth of 0 microns (μm), curve 476B shows the temperature of skin 250 at a depth of 5 μm, and curve 476C shows the temperature of skin 250 at a depth of 10 μm. Curves 472A, 472B, and 472C relate to stratum corneum layer 252. Accordingly, the temperature of stratum corneum layer 252 increases dramatically in response to the heating stage, and is maintained at a high temperature, ranging from 400° C. to 340° C. Curve 476D shows the temperature of skin 250 at a depth of 30 μm. At this depth, the temperature of the skin rises far more gradually, and does not exceed 250° C. Curve 476E shows the temperature of skin 250 at a depth of 100 μm. At this depth, the temperature of the skin barely rises, reaching 50° C.

Reference is now made to FIG. 4G which shows a temperature gradient, generally referenced 478, of skin 250 at various depths during the heating stage by protrusion 338 (FIG. 3A) of dermal condition device 300 (FIG. 3A) for a pulse of 8 ms, constructed and operative in accordance with another embodiment of the disclosed technique. Although the effect on skin 250 is illustrated respective of dermal condition device 300 (FIG. 3A), this is not meant to be limiting and it is to be understood that a similar effect is produced on skin 250 by applying the heating stage by dermal conditioning device 200. Dashed line 482 indicates the border between stratum corneum layer 252 and deeper skin layers 254, 256, and 258. The indications of the skin depths are intended as exemplary only, and are not to scale. The heat gradient of the region above dashed line 482 corresponds to curves 476A, 476B, and 476C of FIG. 4F. The heat gradient of the region below dashed line 482 corresponds to curves 476D, and 476E of FIG. 4F. Thus, the heating stage has a dual effect on skin 250. Stratum corneum layer 252 is heated to a relatively high temperature, as shown by curves 476A, 476B, and 476C (FIG. 4F), affecting its elasticity. When stratum corneum layer 252 is at a relative humidity of 100% prior to the heating stage, its elongation in response to an applied stress is 200%. However, when stratum corneum layer 252 is at a relative humidity approaching 0% after the heating stage, its elongation in response to an applied stress decreases to less than 10%, as illustrated in FIG. 4E. By contrast, deeper skin layers 254, 256, and 258 are heated to a lower temperature, as shown by curves 476D and 476E (FIG. 4F).

Reference is now made to FIG. 4H, generally referenced 480, which shows area of skin 10 (FIG. 1A) after undergoing an ablative treatment in accordance with prior art methods. Following the ablative treatment, a portion of stratum corneum 12A has been removed, as indicated by label 482, "Removal of the SC". Furthermore, the ablation has caused a coagulated zone 12E to form between the area external to skin 10, above stratum corneum layer 12A, and the deeper skin layers 12F, corresponding to deeper skin layers 128, 12C, an 12D (FIG. 1A), where the viable tissue lies. Coagulated zone 12E seals deeper skin layers 12F from the area external to skin 10, above stratum corneum layer 12A. Consequently, a solution applied externally to skin 10 collects in a reservoir, indicated as 12G, and is not absorbed by deeper skin layers 12F.

Reference is now made to FIG. 4I, generally referenced 490, which shows area of skin 250 (FIG. 4A) after undergoing the non-ablative treatment by dermal conditioning device 200 of FIG. 2A, constructed and operative in accordance with another embodiment of the disclosed technique. In contrast with area of skin 10 of FIG. 4H, following the non-ablative treatment by dermal conditioning device 200 (FIG. 2A), stratum corneum layer 252 has been perforated slightly, leaving free passage zones 492 and 494, corresponding to free passage zones 262 and 264 (FIG. 4A). Perforated stratum corneum layer 252 does not pose a barrier to deeper skin layers 496, corresponding to deeper skin layers 254, 256, and 258 (FIG. 4A). Furthermore, the relatively small volume of coagulated tissue 498, resulting from the controlled application of low levels of heat energy by dermal conditioning device 200, poses only a very limited obstacle for material to pass from the external surface of skin 250, above stratum corneum layer 252, to deeper skin layers 496. Finally, the dehydration of stratum corneum layer 252 and deeper skin layers 496 results in the formation of a water concentration gradient between a solution introduced to the external surface of stratum corneum layer 252 and deeper skin layers 496. This concentration gradient is greater than a concentration gradient that might present in other areas of skin 250 that have not undergone treated by dermal conditioning device 200. The combination of these effects—perforation, limited coagulation, and dehydration—on skin 250 provide free passages for the solution from the external surface of stratum corneum layer 252 into dehydrated deeper skin layers 496, resulting in rapid absorption. It may be noted that the perforations in stratum corneum layer 252 and small volume of coagulated tissue 498 provide free passage and rapid absorption for hydrophobic and lipoliphic solutions into deeper skin layers 496 as well.

Figure 5C:
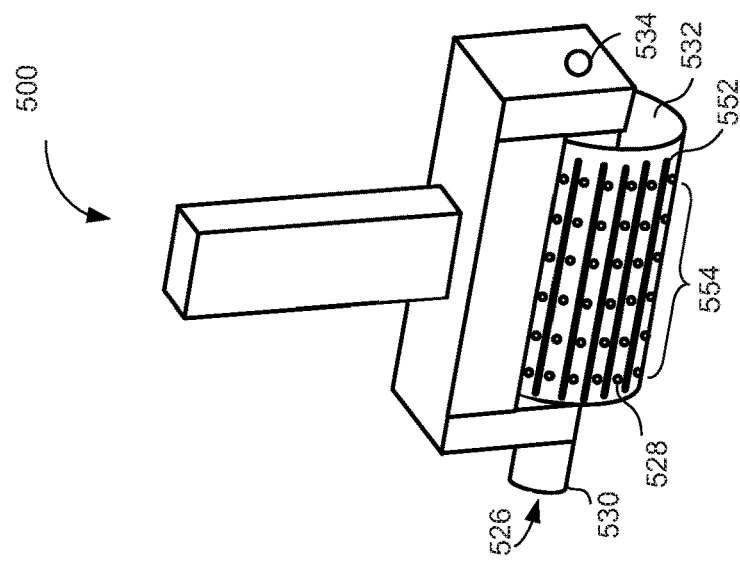
FIGS. 5A-5C are schematic illustrations of a dermal conditioning device of the disclosed technique that produces heat using an optical emitter, constructed and operative in accordance with another embodiment of the disclosed technique.
Figure 5B:
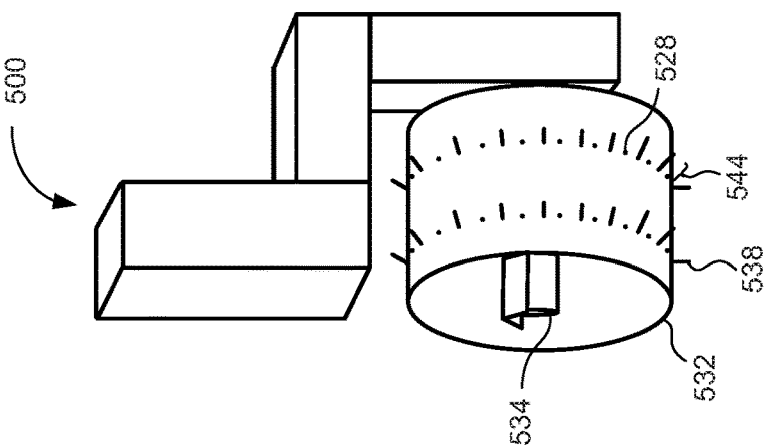
Figure 5A:
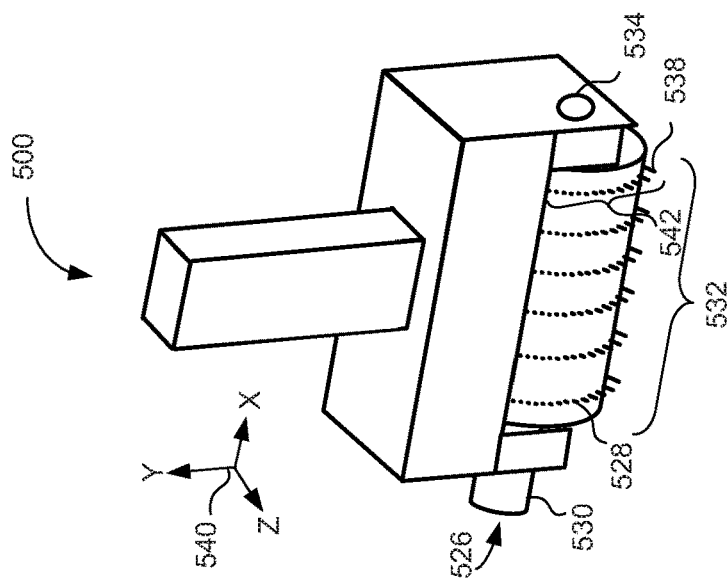

Reference is now made to FIGS. 5A-5C which are schematic illustrations of a dermal conditioning device of the disclosed technique that produces heat using an optical emitter, generally referenced 500, constructed and operative in accordance with another embodiment of the disclosed technique. Dermal conditioning device 500 produces heat using an optical emitter, and generates stress by use of a rotatable cylinder that is operative to roll over the surface of the skin (not shown), and produce a strain on the skin. In the description that follows, dermal conditioning device 500 is understood to include at least the hardware components of dermal conditioning device 200 (FIGS. 2A-2E) and is operable to perform any of the procedures and functions described above with respect to skin 250. Dermal conditioning device 500 includes a controller (not shown) and a power supply (not shown), an actuator 530 and a roller 532 as well as a heat generator 526 and a heat emitter 528. The controller and the power supply correspond to controller 208 and power supply 210 (both from FIG. 2B). Heat generator 526 and heat emitter 528 correspond to heat generator 226 and heat emitter 228 (both from FIG. 2B). Actuator 530 and roller 532 correspond to actuator 230 and stress conveyor 232 (both from FIG. 2B). The controller, the power supply and heater 526 may be integrated within the body of dermal conditioning device 500.

Roller 532 is a rotatable cylinder that forms the distal end of dermal conditioning device 500 and is operative to directly contact and touch skin 250. Actuator 530 is electrically coupled to the power supply and the controller. Actuator 530 is mechanically coupled to roller 532 via a shaft 534. Shaft 534 is oriented orthogonally to the longitudinal y-axis of dermal conditioning device 500 and is positioned through a central axis of rotation parallel to the x-axis of dermal conditioning device of roller 532, thereby enabling roller 532 to rotate about shaft 534. An axis guide 540 of dermal conditioning device is shown in FIGS. 5A-5C. Actuator 530 can be embodied as a rotatable motor operative to rotate roller 532 about shaft 534.

Heat emitter 528 is formed of multiple channels that couple heat generator 526 to the distal end of dermal conditioning device 500 formed by roller 532. Heat generator 526 may be positioned in any suitable location within dermal conditioning device 500 such as inside roller 532. The channels of heat emitter 528 may be arranged in multiple rows forming parallel rings 542 covering the surface of roller 532. Roller 532 may be disposed with 1, 2, 3 . . . n parallel rings 542 of channels forming heat emitter 528. The distance between the rings may range from tens of micrometers to millimeters, such as 0.05 mm, 0.2 mm or 1 mm. The distance between any two of the channels is may range from 0.1 mm to 0.5 mm, from 0.5 mm to 1 mm, from 1 mm to 1.5 mm, from 1.5 mm to 2 mm, from 2 mm to 2.5 mm or from 2.4 mm to 3 mm. All these distances are merely brought as examples.

With reference to FIGS. 5A-5B, dermal conditioning device 500 is shown with heat generator 526 configured as an optical emitter operative to emit light suitable for causing the evaporation of water from live tissue, as described above with respect to FIG. 3C. Heat generator 526 may be an IPL light source, an IR light source or a solid state laser diode and may emit a laser having a wavelength of approximately 2.94 µm. Heat emitter 528 is formed of multiple optical channels that are configured to convey the optical signal emitted by heat generator 526 to the external surface of roller 532 at the distal end of dermal conditioning device 500. The optical signal emitted by heat emitter 528 causes water to evaporate from skin 250. When heat generator 526 is an IPL light source or IR light source, one or more reflectors (not shown) may be mounted between heat generator 526 and heat emitter 528 to concentrate the emitted light to a narrower beam in a range of approximately twice the diameter of each channel of heat emitter 528. When heat generator 526 is a solid state laser, heat generator 526 includes multiple small diameter lasers (not shown), each mounted within one of the optical channels of heat emitter 528.

With reference to FIG. 5A, heat emitter 528 is constructed as multiple optical channels embedded within multiple protrusions 538 covering roller 532. Heat generator 526 and heat emitter 528 of dermal conditioning device 500 are substantially similar to heat generator 326 (FIG. 3C) and heat emitter 328 (FIG. 3C) of dermal conditioning device 300 (FIG. 3C), with the notable difference that heat generator 526 and heat emitter 528 are disposed on the surface of roller 532. Protrusions 538 may be formed of any suitable biocompatible, thermally conductive and thermally resilient material, such as described above with respect to array of protrusions 338 (FIG. 3B). Similarly, the dimensions, shape and material of protrusions 538 and the distances there between may correspond to those of protrusions 338 of dermal conditioning device 300. Plurality of protrusions 538 depress the is surface of skin 250 in a non-invasive manner, in synchrony with the rotation of roller about shaft 534. Protrusions 338 are sufficiently dull so as to not penetrate skin 250 when treated by dermal conditioning device 500, and depress skin 250 to a depth ranging from 0.1 millimeters (mm) to 1 mm, or from 0.05 to 1.2 mm, or from 0.2 mm to 0.8 mm, or from 0.3 mm to 0.7 mm, or from 0.4 to 0.6 mm. In one embodiment, the diameter of each of array of protrusions 338 may range from being 0.05 mm, 0.1 mm, 0.15 mm and up to 1.0 mm. The height of protrusions 338, as measured from the outer perimeter of roller 532 may range from being 0.05 mm, 0.1 mm, 0.15 mm and up to 1.0 mm. Although protrusions 338 are shown as pins in FIGS. 5A-5B, they may have any suitable shape for applying stress to the skin, such as the pyramid shape described above with respect to FIGS. 3A-3C.

With reference to FIG. 5B, heat emitter 528 is configured as multiple optical channels embedded directly on surface roller 532, between protrusions 538. Thus, during treatment, there is a small distance, indicated so via reference number 544, corresponding to the height of protrusions 538, between heat emitter 528 and the surface of the stratum corneum. The embodiments shown in FIGS. 5A-5B are intended for illustrative purposes. Thus, features such as the handle and housing for dermal conditioning device 500 are shown as conceptual illustrations only. Whereas the optical channels forming heat emitter 528 of dermal conditioning device 500 of FIG. 5A are embedded within plurality of protrusions 538, the optical channels forming heat emitter 528 of dermal conditioning device 500 of FIG. 5B are disposed on the surface of roller 532, in between plurality of protrusions 538. Thus, the areas of the skin directly affected by heat emitter 528 of FIG. 5A correspond to those areas of skin directly affected by plurality of protrusions 538. Furthermore, heat emitter 528 of dermal conditioning device 500 of FIG. 5A comes in direct contact with the skin. By contrast, the areas of the skin directly affected by heat emitter 528 of dermal conditioning device 500 of FIG. 5B are in between those areas of skin directly affected by plurality of protrusions 538. Furthermore, heat emitter 528 may not come in direct contact with the skin by a distance corresponding to the height of plurality of protrusions 538.

Reference is now made to FIG. 5C which shows a further embodiment for dermal conditioning device 500, constructed and operative in accordance with embodiment of the disclosed technique. In this implementation for dermal conditioning device 500, stress applier 552, corresponding to stress applier 232 (FIG. 2B) is formed as multiple elongated ridges spanning the width of roller 532. Heat emitter 528 is formed from multiple optical channels embedded directly on roller 532 and arranged into rows 554 spanning the width of roller 532. Rows 554 of heat emitter 528 are interleaved with the ridges of stress applier 552. The width of roller 532 may range from 0.5 cm to 4 cm. The rows 554 of channels forming heat emitter 528 are positioned in between the elongated ridges 552. The height of ridges 552 may range from 0.5 mm to 2 mm from the surface of roller 532. In one embodiment, the height of ridges 552 of FIG. 5C may be approximately 1.25 mm, similar to the dimensions of protrusions 538 of FIG. 3B. Similarly, ridges 552 of FIG. 5C may be made of a suitable thermally conductive and biocompatible material as protrusions 338 (FIG. 3B).

The rotation of roller 532 by actuator 530 determines the exposure time of area of skin 250 to light emitted by heat generator 526. Thus, the level of epidermis dehydration of the skin is a function of the rotational frequency of roller 532, as well as the power and wavelength of the optical signal emitted by heat generator 526. The controller (not shown) controls the rotational speed of roller 532 about shaft 534, as well as the pulse duration and intensity of the light emitted by heat generator 526 to dehydrate the skin while avoiding ablation, according to the disclosed technique. In the case of heat generator 526 being embodied as an IPL or solid state laser, the controller may synchronize the light pulse emitted by heater 526 with the rotational speed of actuator 538, to ensure that light is emitted only from the optical channels of heat emitter 528 while within a line-of-sight with area of skin 250. Controller 508 controls the velocity of roller 532 over the skin. For example the velocity may range from 1 mm/s to 5 mm/s. With respect to FIGS. 5A-5B, the combination of the spacing between the optical channels of heat emitter 528 on roller 532 together with the rotational frequency of roller 532, as controlled by the controller is calibrated such that at any given time, the temperature of the contact areas of skin 250 with any one of protrusions 538 is substantially affected by a single one of protrusions 538, such that there are regions in between the areas of the skin making contact with protrusions 538 that remain at normal human body temperature of 37° C. Similarly, with respect to FIG. 5C, the combination of the spacing between the optical channels of heat emitter 528 on roller 532 together with the rotational frequency of roller 532, as controlled by the controller is calibrated such that at any given time, the temperature of the contact areas of skin 250 with any one of ridges 552 is substantially affected by a single one of ridges 552, such that there are regions in between the areas of the skin making contact with ridges 552 that remain at normal human body temperature of 37° C.

After the skin has been dehydrated, such as may be determined by a timer, a sensor, and the like, the controller controls the rotation of roller 532 to cause any of protrusions 538 (FIGS. 5A-5B), or alternatively ridges 552 (FIG. 5C) to apply a non-invasive compression load, or stress on the dehydrated skin, producing a strain on the skin that causes a plurality of fissures to form. The controller calibrates and controls the rotational speed of roller 532 and the subsequent pressure exerted by protrusions 538 (FIGS. 5A-5B), or alternatively by ridges 552 (FIG. 5C) on the skin so as to not puncture or penetrate the skin. As a result, the conditioning of skin 250 by dermal conditioning device 500 is non-invasive. It may be noted that the dehydration of the skin, and the application of stress on the skin by dermal conditioning device 500 may be performed simultaneously, or sequentially, as controlled by the controller. By driving the rotation of roller 532 via actuator 530, and controlling the operation of heater 526, the controller controls the combined application of the heat and stress onto the skin producing the subsequent strain on the skin, and causing the fissuring of the stratum corneum.

Figure 5D:
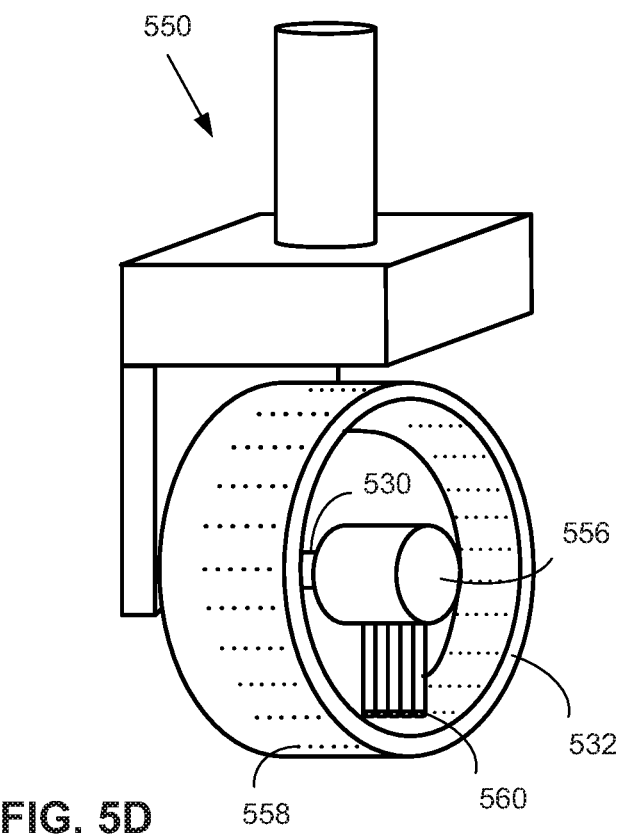
FIGS. 5D-5E are schematic illustrations of a dermal conditioning device of the disclosed technique that produces heat using a dry flow, constructed and operative in accordance with a further embodiment of the disclosed technique.
Figure 5E:
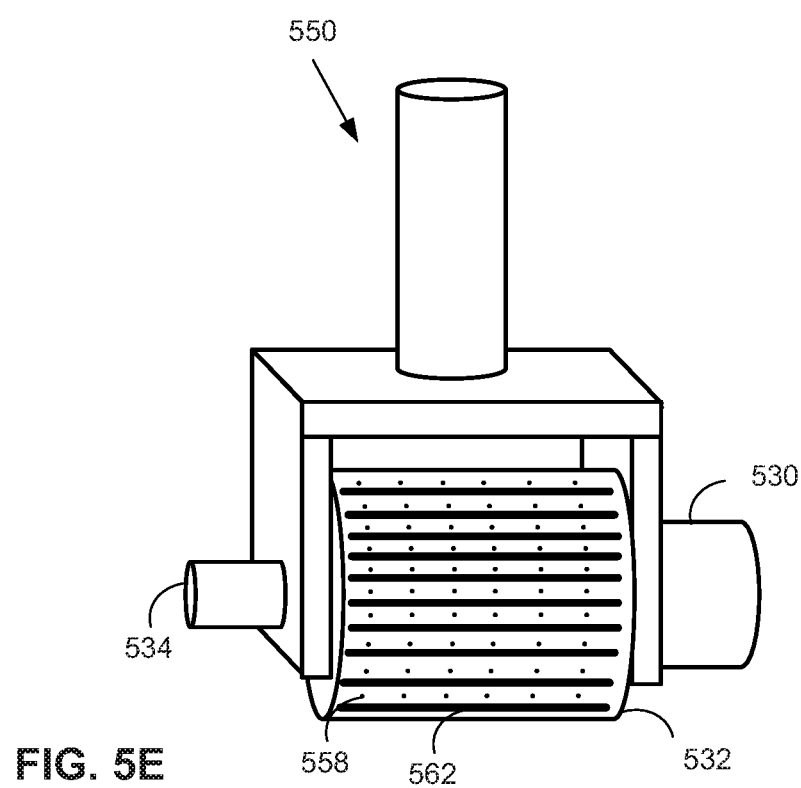

Reference is now made to FIGS. 5D-5E, which are schematic illustrations of a dermal conditioning device of the disclosed technique that produces heat using a dry flow, generally referenced 550, constructed and operative in accordance with a further embodiment of the disclosed technique. Dermal conditioning device 550 is understood to include at least the hardware components of dermal conditioning device 200 (FIGS. 2A-2E) and is operable to perform any of the procedures and functions described above with respect to skin 250. Dermal conditioning device 550 is substantially similar to dermal conditioning device 500 of FIGS. 5A-5C, having a roller 532 and an actuator 530 that operate as described above. Dermal conditioning device 550 includes a heat generator 556 and a heat emitter 558 coupled via a manifold 560. Manifold 560 along with heat generator 556 and heat emitter 558 together are operative to a cause a flow of dry air or gas, referred to herein as a "dry flow", from heat generator 556 to be expelled from the distal end of dermal conditioning device 550 towards skin 250. The dry flow serves a dual purpose that both dehydrates the stratum corneum and deeper skin levels and additionally applies a stress as a steady fluid pressure, producing a strain on the skin that causes the stratum corneum to fissure. The combined dehydration and application of the stress by roller 532, heat generator 556 and heat emitter 558 may cause peeling of the stratum corneum, further contributing to the dehydration of the deeper skin layers, to condition the viable cells residing therein to subsequently absorb any of a hydrophilic, lipophilic or hydrophobic solution.

Heat emitter 558 is formed of multiple perforations on the surface of roller 532 that channel the dry flow produced by heat generator 556 via manifold 560 to the external surface of roller 532. Heat generator 556 generates the dry flow, for example by using an air dryer that heats air to a temperature ranging from 30° C. to 600° C. Manifold 560, illustrated as a plurality of tubes, channels the dry flow from heat generator 556 to roller 532, where the dry flow is expelled heat emitter 558, shown as perforations (not labeled) on the surface of roller 532. In some embodiments, the size of manifold 560 may range from being 0.5 mm and 0.6 mm up to 3 mm. The diameter of the perforations of heat emitter 558 on the outer surface of roller 532 may range from being 0.5 mm up to 0.1 mm. The perforations of heat emitter 558 are aligned on the surface of roller 532 as multiple parallel rows or parallel rings. The distance between the perforations within a row may range from between 0.1 mm up to 3 mm. The distance between the rows may range from between 0.5 mm up to 3 mm.

In addition to the pressure exerted on the skin from the dry flow, roller 532 is operable to apply pressure on the surface of the skin. Thus the stress imposed on the skin is a combination of both the dry flow and the pressure from roller 532. The controller controls the timing, temperature and pressure of the dry flow and the rotational speed of roller 532 about shaft 534, thereby controlling the level of heat and stress delivered to the skin and the resulting strain produced on the skin. The level of heat is calibrated to cause sufficient dehydration of the skin to create fissures, without inducing trauma, as described in the heat calculations given above in equations 6-13.

With reference to FIG. 5E, another embodiment of dermal conditioning device 550 is shown, constructed and operative in accordance with an embodiment of the disclosed technique. In this embodiment for dermal conditioning device 550, roller 532 is additionally provided with one or more ridges 562 spanning the width of roller 532, such as described above with respect to FIG. 5C. The rows of channels forming heat emitter 558 are positioned in between the elongated ridges 562. In some embodiments, the velocity of roller 532 over the skin may range from 1 mm/s to 5 mm/s. The temperature of the dry flow emitted from dermal conditioning device 500 may range from 10° C. to 50° C. The humidity of the dry flow emitted from dermal conditioning device 550 may range from 0% to 10% humidity.

Reference is now made to FIGS. 6A-6B which are schematic illustrations of a dermal conditioning device of the disclosed technique that produces heat using an RF emitter, generally referenced 600A and 600B, respectively, constructed and operative in accordance with another embodiment of the disclosed technique. FIG. 6A illustrates an embodiment using a mono-polar electrode and FIG. 6B illustrates an embodiment using a set of bi-polar electrodes. In the description that follows, dermal conditioning device 600 is understood to include at least the hardware components of device 200 of FIGS. 2A-2E and is operable to perform any of the procedures and functions described above with respect to skin 250. In particular, dermal conditioning devices 600A and 66B each include a housing 620, a controller 608, a power supply 610, a linear motor 630, an RF generator 626 and either a single electrode 628A (FIG. 6A) or a pair of electrodes 628B (FIG. 68), and a communications bus 616. Controller 608 corresponds to controller 208 (FIG. 2B), power supply 610 corresponds to power supply 210 (FIG. 2A), linear motor 630 corresponds to actuator 230 (FIG. 28), RF generator 626 corresponds to heat generator (FIG. 2B), single electrode 628 of FIG. 6A corresponds to heat emitter 228 (FIG. 2B) and pair of electrodes 628B (FIG. 6B) corresponds to heat emitter 228 (FIG. 2B). Controller 608, power supply 610, motor 630 and RF generator 626 are integrated within housing 620 of respective dermal conditioning devices 600A and 600B. Electrode 628A of FIG. 6A is a mono-polar electrode whereas electrodes 628B of FIG. 6B are a set of bi-polar electrodes. Controller 808, power supply 610, motor 630 and RF generator 626 are electrically coupled via communications bus 616.

With reference to FIG. 6A, electrode 628A is electrically coupled to motor 630 and RF generator 626 of dermal conditioning device 600A. Electrode 628A is disposed at the distal end of dermal conditioning device 600A. Motor 630 is a linear motor that is operative to lightly push electrode 628A against skin 250, thereby applying a stress to dehydrated skin 250 to produce a strain causing the formation of fissures on the surface of skin 250. RF generator 626 produces a high frequency alternating electrical current that agitates the ions within stratum corneum layer 262 and deeper skin layers 254, 256 and 258, resulting in the heating of water stored therein via frictional heat, as indicated by dashed region 632A. In accordance with experimental results that have shown that water begins evaporating from tissue starting from a tissue temperature of 70° C. and approximately half of the tissue water content is lost when the tissue temperature reaches 104° C., controller 608 controls the heating of stratum corneum layer 252, and deeper skin layers 254, 256 and 258 via RF generator 626 to heat skin 250 to a temperature of up to 100° C. Controller 608 controls the pulse duration of the RF signal emitted by RF generator 604A to between 30-50 seconds. At this rate, the expected rise in temperature of skin 250 is substantially low. The maximal power delivered to skin 250 is approximately 25 W/m$^{2\circ}$ K with a frequency range of 460 KHz. When a single electrode is used, the heat penetrates a narrow, deep region, i.e. reaching into stratum spinosum layer 256. The combination of precisely controlled heating and application of stress causes the formation of fissures in stratum corneum layer 252 without substantially compromising or altering the previously existing immune and intact state of skin 250.

With reference to FIG. 6B, electrodes 628B are electrically coupled to motor 630 and RF generator 626 of dermal conditioning device 600B. Electrodes 628B are disposed at the distal end of dermal conditioning device 600B. Motor 630 is a linear motor that is operative to lightly push electrodes 6288 against skin 250, thereby applying a stress to dehydrated skin 250, to produce a strain causing the formation of fissures on the surface of skin 250. The combination of precisely controlled heating and application of stress causes the formation of fissures in stratum corneum layer 252 without substantially compromising or altering the previously existing immune and intact state of skin 250. RF generator 626 produces a high frequency alternating electrical current that agitates the ions within stratum corneum layer 252 and deeper skin layers 254, 256 and 258, resulting in the heating of water stored therein via frictional heat, as indicated by dashed region 632B. Controller 608 controls the heating of stratum corneum layer 252 and deeper skin layers 254, 256 and 258 via RF generator 626 to heat skin 250 to a temperature of up to 100° C. Controller 608 controls the pulse duration of the RF signal emitted by RF generator 604A to between 30-50 seconds. At this rate, the expected rise in temperature of skin 250 is substantially low. The maximal power delivered to skin 250 is approximately 25 W/m$^{2\circ}$ K with a frequency range of 460 KHz. When two electrodes are used, the heat penetrates a wide shallow region as shown in FIG. 6B, i.e. the heat does not penetrate beyond stratum granulosum layer 254. The combination of precisely controlled heating and application of stress causes the formation of fissures in stratum corneum layer 252 without substantially compromising or altering the previously existing immune and intact state of skin 250.

Figure 7:
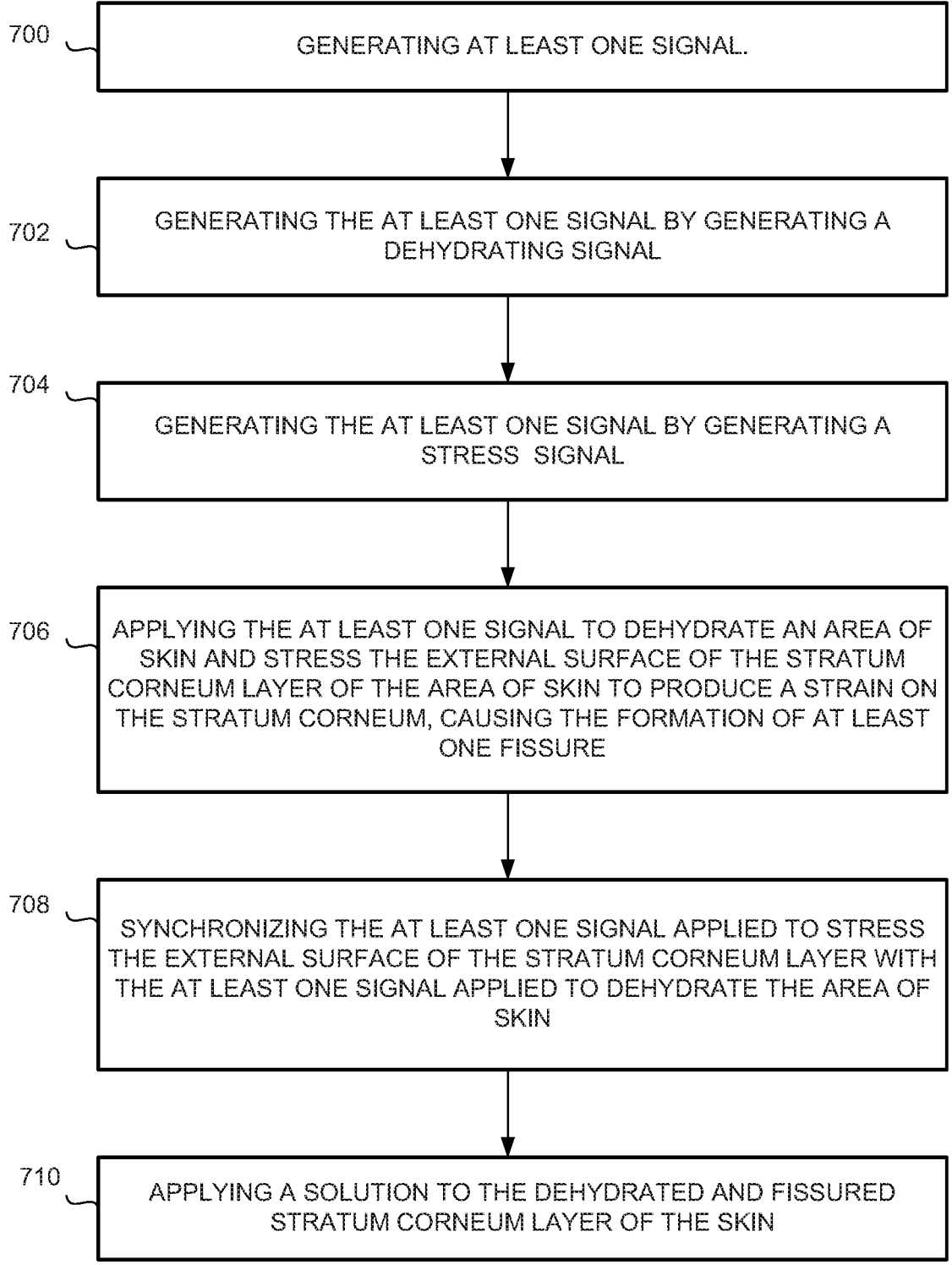
FIG. 7 is a schematic illustration of a method for operating a dermal conditioning device, constructed and operative in accordance with a further embodiment of the disclosed technique.

Reference is now made to FIG. 7 which is a schematic illustration of a method for operating a dermal conditioning device, operative in accordance with a further embodiment of the disclosed technique. In a procedure 700, at least one signal is generated. With reference to FIG. 2A, controller 208 controls the generating of at least one signal by heater 204 and by stressor 206. Controller 208 controls any of the timing, intensity, a temperature, a frequency, duration, and a phase, of the at least one signal. In one embodiment heater 204 and stressor 206 are separate components. With reference to FIG. 3A, controller 308 controls the generation of heat by heater 304 and controller controls the generation of stress by stressor 306. Heater 304 may maintain the distal end of dermal conditioning device 300 at 400 degrees Celsius. Stressor 306 may generate a pulse of a duration ranging between: 8 milliseconds (ms) and 14 ms, or between 5 ms and 15 ms, or between 5 ms and 20 ms, or between 8 ms and 20 ms. In another embodiment, heater 204 and stressor 206 are implemented as a single component. With reference to FIGS. 5D-5E, controller 508 controls the generation of a dry flow by heat generator 556.

In procedure 702 generating the at least one signal generates a dehydrating signal. Generating the dehydrating signal includes performing one or more of: generating a dry flow, generating an RF signal, generating an optical signal, and generating a thermal heating signal. The dehydrating signal is applied to dehydrate the area of skin. With reference to FIGS. 5-5E, heat generator 556 generates a dry flow that dehydrates stratum corneum layer 252 and deeper skin layers 254, 256 and 258. With reference to FIGS. 6A-68, RF generator 626 generates a high frequency alternating electrical current that agitates the ions within stratum corneum layer 252 and deeper skin layers 254, 256 and 258, resulting in the heating of water stored therein via frictional heat. With reference to FIGS. 5A-5C, heat generator 526 emits a laser having a wavelength of approximately 2.94 μm, corresponding to the maximum absorption peak of water. Heat emitter 528 emits the optical signal emitted by heat generator 526 onto skin 250, causing water to evaporate from skin 250. With reference to FIGS. 3A-3C, heat generator 326 generates thermal heat that is transferred to the distal end of dermal conditioning device 300. For example heat generator 326 may be a ceramic heater that is thermally coupled to a thermally conducting surface 328 on the distal end of dermal conditioning device 300. The thermal heat causes water to evaporate from skin 250.

In procedure 704 generating the at least one signal generates a is stress signal, where generating the stress signal includes performing any of: generating a dry flow, generating a radio frequency signal, generating a series of mechanical pulses, and generating a mechanical rotation. The stress is applied non-invasively to depress the external surface of the stratum corneum layer. In some embodiments the external surface of the stratum corneum layer is depressed to a depth ranging between 0.1 millimeters and 1 millimeter, or from 0.05 to 1.2 mm, or from 0.2 mm to 0.8 mm, or from 0.3 mm to 0.7 mm, or from 0.4 to 0.6 mm. With reference to FIGS. 5D-5E, heat generator 556 generates a dry flow that imposes a stress on stratum corneum layer 252. With reference to FIGS. 6A-6B, RF generator 626 generates a high frequency alternating electrical current that imposes a stress on stratum corneum layer 252. With reference to FIGS. 3A-3C, actuator 330 advances and retracts actuator tip 332 in a harmonic pulsating motion in accordance with a predefined pulse duration and a predefined number of pulses per treatment, as controlled by controller 308. Plurality of protrusions 338 depress the surface of skin 250 in a non-invasive manner, in synchrony with the pulsating motion. The depression depth ranges between 0.1 millimeters (mm) to 1 mm, or from 0.05 to 1.2 mm, or from 02 mm to 0.8 mm, or from 0.3 mm to 0.7 mm, or from 0.4 to 0.6 mm. With reference to FIGS. 5D-5E, actuator 530 is mechanically coupled to roller 532 via shaft 534. Actuator 530 is a rotatable motor that causes roller 532 to rotate about shaft 534. Plurality of protrusions 538 depress the surface of skin 250 in a non-invasive manner, in synchrony with the rotation of roller about shaft 534.

In a procedure 706, the at least one signal is applied to dehydrate the area of skin, and to stress the external surface of a stratum corneum layer of the area of skin. The stress is calibrated to produce a strain on the stratum corneum layer of the area of skin. The strain causes a formation of at least one fissure in the stratum corneum layer of the area of skin when the area of skin is dehydrated, while maintaining a pre-fissure immune status of the area of skin. With reference to FIG. 2A, controller controls heater 204 to generate heat in accordance with one or more heat parameters, as defined by equations 6-13 above. Heater 204 produces heat and applies the heat to the external surface of stratum corneum layer 252 of skin 250, thereby causing water stored therein to evaporate. In one embodiment, stratum corneum layer 252 of area of skin 250 is dehydrated to less than 10% water content. In another embodiment, stratum granulosum layer 254 of area of skin 250 is dehydrated to less than 70% water content. Controller 208 additionally controls non-invasive stressor 206 to generate a stress in accordance with one or more stress control parameters. Stressor 206 produces the stress and applies the stress externally to stratum corneum layer 252. The externally applied stress is non-invasive and causes a strain on dehydrated stratum corneum layer 252 which cracks the dehydrated stratum corneum layer 252 causing the formation of plurality of fissures 260 in stratum corneum layer 252, while preserving the pre-fissure immune status of area of skin 250.

In a procedure 708, the at least one signal applied to stress the external surface of the stratum corneum layer of the area of skin is synchronized with the at least one signal applied to dehydrate the area of skin. With reference to FIG. 31, controller 308 synchronizes the harmonic pulsating motion of actuator tip 332 with the emission of the light by heat generator 326.

In procedure 710, a solution is applied to the dehydrated and fissured stratum corneum layer of the skin. With reference to FIG. 4A, a solution (not shown) is applied to fissured stratum corneum layer 252 of skin 250, where it is absorbed by deeper skin layers 254, 256, and 258.

In some embodiments of the disclosed technique, generating the at least one signal further includes controlling any of a timing, an intensity, a temperature, a frequency, a duration and a phase of the at least one signal. With reference to FIG. 2A, controller 208 controls any of the timing, intensity, a temperature, a frequency, duration and a phase of a signal generated by any of heater 204 and stressor 206.

It will be appreciated by persons skilled in the art that the various embodiments disclosed herein above are intended as exemplary. The disclosed technique is not limited to the specific combinations and permutations of the elements described above. In particular, additional embodiments for a heater, a heat generator, a heat emitter, a stressor, an actuator and a stress applier, as are known in the art, may be combined in any suitable manner to achieve the disclosed technique.

It will be appreciated by persons skilled in the art that the disclosed technique is not limited to what has been particularly shown and described hereinabove. Rather the scope of the disclosed technique is defined only by the claims, which follow.

The invention claimed is:

1. A dermal conditioning device for creating at least one fissure in a stratum corneum layer of an area of skin, comprising:
   at least one non-invasive skin fissuring generator;
   at least one controller coupled to said at least one non-invasive skin fissuring generator;
   a power supply coupled to said at least one non-invasive skin fissuring generator and said at least one controller;
   a housing encasing said at least one non-invasive skin fissuring generator and said at least one controller; and
   at least one dull tip forming a distal end of said dermal conditioning device, said at least one dull tip mechanically coupled to said housing and electrically coupled to said at least one non-invasive skin fissuring generator, wherein said at least one dull tip is sufficiently dull to depress said surface of said area of skin without penetrating said stratum corneum layer of said area of skin when said at least one dull tip is in physical contact with said surface of said area of skin,
   wherein said at least one controller controls said at least one non-invasive skin fissuring generator to generate at least one signal calibrated to:
   a) maintain said at least one dull tip at a substantially constant temperature and transfer an amount of heat to said area of skin via said at least one dull tip over a pulse duration that maintains the surface temperature of said area of skin as a function of said pulse duration, wherein said amount of heat is calibrated to dehydrate said area of skin of said stratum corneum layer while maintaining viability of a stratum granulosum layer, a stratum spinosum layer and a stratum basale layer of said area of skin, and
   b) stress the surface of said dehydrated area of skin of said stratum corneum layer via said at least one dull tip, wherein said at least one signal is calibrated to produce a strain on said stratum corneum layer of said area of skin to only cause a formation of at least one fissure in said stratum corneum layer of said area of skin without inducing trauma, and maintain a pre-fissure immune status of said area of skin; and
   wherein said at least one controller is configured to synchronize, with respect to said pulse duration, said transferring of said amount of heat to said area of skin via said at least one dull tip with said stressing of the surface of said dehydrated area of skin via said at least one dull tip.

2. The dermal conditioning device according to claim 1, wherein said amount of heat is calibrated to dehydrate said stratum corneum layer of said area of skin to less than 10% water content.

3. The dermal conditioning device according to claim 1, wherein said amount of heat is calibrated to dehydrate a stratum granulosum layer of said area of skin to less than 70% water content.

4. The dermal conditioning device according to claim 1, wherein said substantially constant temperature does not exceed 400 degrees Celsius.

5. The dermal conditioning device according to claim 1, wherein said pulse duration does not exceed 14 milliseconds.

6. The dermal conditioning device according to claim 1, wherein said controller controls a parameter of said at least one signal, said parameter selected from the group consisting of: a timing; an intensity; a frequency; a duration; and a phase, of said at least one signal.

7. The dermal conditioning device according to claim 1, wherein said at least one non-invasive skin fissuring generator comprises a dehydrating generator selected from the group consisting of:
   i. an optical emitter; and
   ii. a thermal heater.

8. The dermal conditioning device according to claim 1, wherein said at least one non-invasive skin fissuring generator comprises a motor, and wherein said at least one signal stresses the surface of said dehydrated area of skin via said at least one dull tip by pushing said at least one dull tip distally and retrieving said at least one dull tip proximally.

9. The dermal conditioning device according to claim 1, wherein said at least one dull tip comprises at least one non-invasive dull protrusion selected from the group consisting of: a ridge, a pyramid shaped tooth, and a pin.

10. The dermal conditioning device according to claim 9, wherein said at least one non-invasive dull protrusion has embedded therein an optical channel, said optical channel configured to transfer said amount of heat to said area of skin via said at least one dull tip.

11. A dermal conditioning device for creating at least one fissure in a stratum corneum layer of an area of skin, comprising:
   a generator configured to generate a dry flow;
   at least one controller, electrically coupled to said generator and configured to control said generating of said dry flow;
   a power supply, coupled to said generator and said at least one controller;
   a housing, encasing said generator and said at least one controller; and
   at least one dry flow emitter, coupled to said generator and disposed at a distal end of said dermal conditioning device, wherein said at least one dry flow emitter is configured to transfer said dry flow to said area of skin,
   wherein said controller calibrates said generating of said dry flow to:
   a) dehydrate said area of skin, via said at least one dry flow emitter, while maintaining viability of a stratum granulosum layer, a stratum spinosum layer and a stratum basale layer of said area of skin, and
   b) apply a stress as a steady fluid pressure to said area of skin via said at least one dry flow emitter, wherein said applied stress is calibrated to produce a strain on said stratum corneum layer of said area of skin to only cause a formation of at least one fissure in said stratum corneum layer of said area of skin without inducing trauma, and maintain a pre-fissure immune status of said area of skin.

12. A method for conditioning an area of skin and creating at least one fissure in a stratum corneum layer, the method comprising the procedures of:
   calibrating an amount of heat corresponding to a substantially constant temperature over a pulse duration;
   generating at least one signal; an-GI applying said at least one signal to:
   i) maintain at least one dull tip of a dermal conditioning device at said substantially constant temperature,
   ii) transfer said amount of heat to said area of skin via said at least one dull tip and maintain the surface temperature of said stratum corneum layer in said area of skin as a function of said pulse duration,
   wherein said amount of heat is calibrated to dehydrate said stratum corneum layer in said area of skin while maintaining viability of a stratum granulosum layer, a stratum spinosum layer and a stratum basale layer of said area of skin, and iii) depress said surface of said dehydrated area of skin of said stratum corneum layer via said at least one dull tip without penetrating said stratum corneum layer of said area of skin in a manner to produce a strain on said stratum corneum layer of said area of skin to only cause a formation of at least one fissure in said stratum corneum layer of said area of skin without inducing trauma, and maintain a pre-fissure immune status of said area of skin; and synchronizing said depressing said surface of said dehydrated area of skin via said at least one dull tip with said transferring said amount of heat to said area of skin via said at least one dull tip.

13. The method according to claim 12, wherein generating said at least one signal generates a dehydrating signal by performing an action selected from the group consisting of: generating an optical signal and generating a thermal heating signal, wherein said at least one dehydrating signal is applied to dehydrate said area of skin.

14. The method according to claim 12, wherein transferring to said area of skin said amount of heat dehydrates said stratum corneum layer of said area of skin to less than 10% water content.

15. The method according to claim 12, wherein transferring to said area of skin said amount of heat dehydrates a stratum granulosum layer of said area of skin to less than 70% water content.

16. The method according to claim 12, wherein said substantially constant temperature does not exceed 400 degrees Celsius.

17. The method according to claim 12, wherein generating said at least one signal that, when applied, depresses said surface of said dehydrated area of skin, comprises generating a series of mechanical pulses.

18. The method according to claim 12, wherein said pulse duration does not exceed 14 milliseconds.

19. The method according to claim 12, wherein depressing said surface of said dehydrated area of skin depresses said dehydrated surface to a depth ranging between 0.1 millimeters and 1 millimeter.

20. The method according to claim 12, wherein generating said at least one signal comprises controlling a first parameter of said at least one signal, said first parameter selected from the group consisting of: a timing; an intensity; a temperature; a frequency; a duration; and a phase, of said at least one signal.

21. The method according to claim 12, further comprising applying a solution to said stratum corneum layer of said area of skin.

22. A method of creating at least one fissure in a stratum corneum layer of an area of skin for transdermal solution delivery, the method comprising:

providing a dermal conditioning device for creating the at least one fissure in the stratum corneum layer of the area of skin for transdermal solution delivery, the dermal conditioning device comprising:

at least one non-invasive skin fissuring generator;

at least one controller coupled to the at least one non-invasive skin fissuring generator;

a power supply coupled to the at least one non-invasive skin fissuring generator and the at least one controller;

a housing encasing the at least one non-invasive skin fissuring generator and the at least one controller; and at least one dull tip forming a distal end of the dermal conditioning device, the at least one dull tip mechanically coupled to the housing and electrically coupled to the at least one non-invasive skin fissuring generator, wherein the at least one dull tip is sufficiently dull to depress the surface of the area of skin without penetrating the stratum corneum layer of the area of skin when the at least one dull tip is in physical contact with the surface of the area of skin, the at least one non-invasive skin fissuring generator comprising a motor, for pushing the at least one dull tip distally and retrieving the at least one dull tip proximally from the area of skin; and controlling, with the at least one controller, the at least one non-invasive skin fissuring generator to generate at least one signal configured to:

(a) maintain the at least one dull tip at a substantially constant temperature and transfer an amount of heat to the area of skin via the at least one dull tip over a pulse duration that maintains the surface temperature of the area of skin as a function of the pulse duration, wherein the amount of heat is calibrated to dehydrate the area of skin while maintaining viability of a stratum granulosum layer, a stratum spinosum layer and a stratum basale layer of the area of skin; and (b) stress the surface of the dehydrated area of skin via the at least one dull tip, via the motor pushing the at least one dull tip distally and retrieving the at least one dull tip proximally from the area of skin, wherein the at least one signal is also configured to produce a strain on the stratum corneum layer of the area of skin to only cause a formation of at least one fissure in the stratum corneum layer of the area of skin without inducing trauma, and maintain a pre-fissure immune status of the area of skin.

* * * * *